(12) United States Patent
Plenderleith et al.

(10) Patent No.: US 12,351,659 B2
(45) Date of Patent: Jul. 8, 2025

(54) CURABLE COMPOSITION COMPRISING A PHOTOINITIATOR

(71) Applicant: Arkema France, Cololmbes (FR)

(72) Inventors: Richard Plenderleith, Wetherby (GB); Jeffrey Klang, Exton, PA (US); Jonathan Andersson, Exton, PA (US); Kangtai Ren, Exton, PA (US); William Wolf, Exton, PA (US); Christopher Macneill, Exton, PA (US)

(73) Assignee: Arkema France, Puteaux (FR)

( * ) Notice: Subject to any disclaimer, the term of this patent is extended or adjusted under 35 U.S.C. 154(b) by 0 days.

(21) Appl. No.: 17/908,556

(22) PCT Filed: Mar. 4, 2021

(86) PCT No.: PCT/EP2021/055529
§ 371 (c)(1),
(2) Date: Sep. 1, 2022

(87) PCT Pub. No.: WO2021/176023
PCT Pub. Date: Sep. 10, 2021

(65) Prior Publication Data
US 2024/0199770 A1    Jun. 20, 2024

(30) Foreign Application Priority Data
Mar. 4, 2020 (EP) .................................. 20305229

(51) Int. Cl.
*C08F 2/50* (2006.01)
*A61K 8/81* (2006.01)
(Continued)

(52) U.S. Cl.
CPC .............. *C08F 2/50* (2013.01); *A61K 8/8152* (2013.01); *A61Q 3/02* (2013.01); *B33Y 70/00* (2014.12);
(Continued)

(58) Field of Classification Search
CPC ...... A61Q 3/02; A61K 8/8152; G03F 7/0037; G03F 7/029; G03F 7/038; G03F 7/028;
(Continued)

(56) References Cited

U.S. PATENT DOCUMENTS

| 6,103,453 A | 8/2000 | Prantl et al. |
| 2008/0199797 A1 | 8/2008 | Sacripante et al. |

(Continued)

FOREIGN PATENT DOCUMENTS

| CN | 20150008708 | 1/2015 |
| CN | 105802482 A | 7/2016 |
| JP | 2017135388 A2 | 8/2017 |
| KR | 20150008708 A | 1/2015 |
| WO | WO2014126830 A2 | 8/2014 |

OTHER PUBLICATIONS

3D Printing Materials—Jun Zhang, Ling Si, Jiquan Yang; Nanjing Normal University Press—4 Pages.

*Primary Examiner* — Monica A Huson
(74) *Attorney, Agent, or Firm* — Christopher R. Lewis

(57) ABSTRACT

The present invention relates to a curable composition comprising an ethylenically unsaturated compound and a specific photoinitiator having dual initiation mechanisms. The invention also relates to a process for the preparation of a cured product, in particular a 3D-printed article, with this composition and to the use of this composition for obtaining an ink, a coating, a sealant, an adhesive, a molded article or a 3D-printed article. The invention further pertains to the use of a specific phosphine oxide photoinitiator in a 3D printing composition or 3D printing process.

27 Claims, 4 Drawing Sheets

(51) Int. Cl.
*A61Q 3/02* (2006.01)
*B33Y 70/00* (2020.01)
*C08F 222/10* (2006.01)
*C08F 222/22* (2006.01)
*G03F 7/029* (2006.01)
*B29C 35/08* (2006.01)
*B29K 33/00* (2006.01)
*B29K 105/16* (2006.01)
*B33Y 10/00* (2015.01)

(52) U.S. Cl.
CPC ........ *C08F 222/104* (2020.02); *C08F 222/22* (2013.01); *G03F 7/029* (2013.01); *B29C 35/0805* (2013.01); *B29C 2035/0827* (2013.01); *B29C 35/0866* (2013.01); *B29C 2035/0877* (2013.01); *B29K 2033/00* (2013.01); *B29K 2105/16* (2013.01); *B33Y 10/00* (2014.12)

(58) Field of Classification Search
CPC ....... B33Y 70/00; B33Y 10/00; C08F 222/22; C08F 222/104; C08F 2/50; B29C 2035/0877; B29C 2035/0827; B29C 35/0866; B29C 35/0805; B29K 2105/16; B29K 2033/00
See application file for complete search history.

(56) References Cited

U.S. PATENT DOCUMENTS

| | | |
|---|---|---|
| 2010/0234484 A1 | 9/2010 | Schellenberg et al. |
| 2015/0203609 A1 | 7/2015 | Anderson et al. |
| 2017/0260418 A1 | 9/2017 | Wu et al. |
| 2019/0049841 A1 | 2/2019 | Okamoto et al. |
| 2019/0169453 A1 | 6/2019 | Sato et al. |
| 2019/0369494 A1 | 12/2019 | Jain et al. |
| 2021/0171760 A1 | 6/2021 | Gupta et al. |

CURABLE COMPOSITION COMPRISING A PHOTOINITIATOR

CROSS-REFERENCE TO RELATED APPLICATIONS

This application is a U.S. national stage application under 35 U.S.C. § 371 of international application number PCT/EP2021/055529, filed Mar. 4, 2021, which claims priority to patent application number EP 20305229.5, filed Mar. 4, 2020.

FIELD OF THE INVENTION

The present invention relates to a curable composition comprising an ethylenically unsaturated compound and a specific photoinitiator having dual initiation mechanisms. The invention also relates to a process for the preparation of a cured product, in particular a 3D-printed article or a nail coating, with this composition and to the use of this composition for obtaining an ink, a coating, a sealant, an adhesive, a molded article or a 3D-printed article. The invention further pertains to the use of a specific phosphine oxide photoinitiator in a 3D printing composition or 3D printing process. The invention further pertains to the use of a specific phosphine oxide photoinitiator in a nail polish composition or nail coating process.

BACKGROUND OF THE INVENTION

In the field of photocure 3D printing there is a growing predominance of printing equipment that use longer wavelength (above 385 nm) light sources to effect curing of the photoactive resin. In formulations designed for use on these printers, phosphine oxide derivatives such as acylphosphine oxides are the preferred class of photoinitiators because of their strong absorbance in the wavelength range of interest. Acylphosphine oxides are classified as Norrish Type I initiators and include the following compounds:

(a) Laromer 819 (also known as Irgacure, 819, Speedcure BPO, or BAPO, namely bis-(2,4,6-trimethylbenzoyl) phenyl phosphine oxide) which has the following structure:

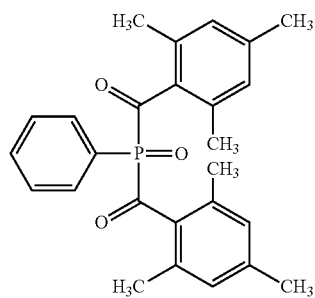 [SMILES: Cc1cc(C)c(C(=O)P(=O)(C(=O)c2c(C)cc(C)cc2C)c2ccccc2)c(C)c1]

(b) Speedcure TPO (also known as 2,4,6-trimethylbenzoyl diphenyl phosphine oxide) which has the following structure:

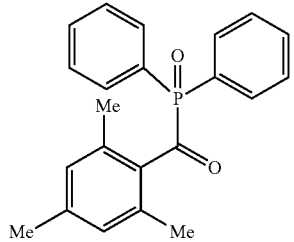 [SMILES: Cc1cc(C)c(C(=O)P(=O)(c2ccccc2)c2ccccc2)c(C)c1]

(c) Speedcure TPO-L (also known as Ethyl (2,4,6-trimethylbenzoyl)phenyl phosphinate) which has the following structure:

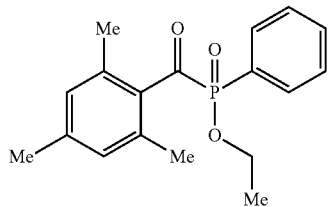 [SMILES: CCOP(=O)(C(=O)c1c(C)cc(C)cc1C)c1ccccc1]

Although existing phosphine oxide initiators are effective and widely used in 3D printing formulations there is a need for initiators that can provide improved cure speed or efficiency and printed parts with enhanced physical properties.

Further, TPO has recently been classified as a Class 1B Reprotoxin based on new toxicology testing. This limits its use in many applications. TPO-L and BAPO are expected to be similarly re-classified in the next 1-2 years. There is thus a need for alternative solutions to these commonly used phosphine oxide photoinitiators which do not have toxicity concerns and use limitations.

Use of phosphine oxide initiators that can exhibit both Norrish Type I and Norrish Type II initiation mechanisms could provide solutions for these needs.

Initiators of this type are disclosed in WO 2014/016567.

SUMMARY OF THE INVENTION

A first aspect of the invention is a curable composition comprising
a) an ethylenically unsaturated compound; and
b) a phosphine oxide photoinitiator having both Norrish Type I and Norrish type II activity.

Another aspect of the invention is a process for the preparation of a cured product, comprising curing the composition according to the invention.

Yet another aspect of the invention is a cured product obtained by curing the composition according to the invention.

Another aspect of the invention is the use of the composition according to the invention for obtaining an ink, a coating, a sealant, an adhesive, a molded article or a 3D-printed article.

Yet another aspect of the invention is the use of a phosphine oxide photoinitiator having both Norrish Type I and Norrish type II activity in a 3D printing composition or in a 3D printing process.

Yet another aspect of the invention is the use of a phosphine oxide photoinitiator having both Norrish Type I and Norrish type II activity in a nail polish composition or in a nail coating process.

DETAILED DESCRIPTION OF THE INVENTION

Figure 1:
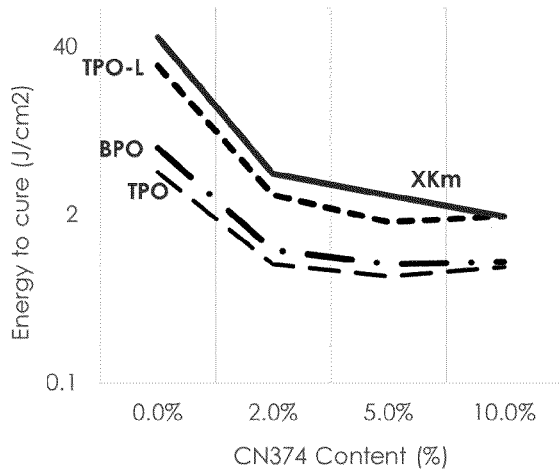
FIG. 1 shows the critical exposure (Ec) for the formulations of Example 2.

In the present application, the term "comprise(s) a/an" means "comprise(s) one or more".

Unless mentioned otherwise, the % by weight in a compound or a composition are expressed based on the weight of the compound, respectively of the composition.

The term «alkyl» means a monovalent saturated alicyclic hydrocarbon radical of formula —$C_nH_{2n+1}$. An alkyl may be linear or branched. A «C1-C20 alkyl» means an alkyl having 1 to 20 carbon atoms.

Examples of alkyl groups include methyl, ethyl, propyl, isopropyl, butyl, isobutyl, tert-butyl, pentyl and hexyl.

The term «alkylaryl» means an alkyl substituted by an aryl group. A «C7-C20 alkylaryl» means an alkylaryl having 7 to 20 carbon atoms. An example of an alkylaryl group is benzyl (—$CH_2$-Phenyl).

The term «halogen» means an atom selected from Cl, Br and I.

The term «alkylene» means a divalent saturated alicyclic hydrocarbon radical of formula —$C_nH_{2n}$—. An alkylene may be linear or branched. A «C1-C20 alkylene» means an alkylene having 1 to 20 carbon atoms.

The term «alkenyl» means a monovalent unsaturated alicyclic hydrocarbon radical. An alkenyl may be linear or branched. A «C2-C20 alkenyl» means an alkenyl having 2 to 20 carbon atoms.

The term «cycloalkyl» means a monovalent saturated alicyclic hydrocarbon radical comprising a cycle. A «C3-C8 cycloalkyl» means a cycloalkyl having 3 to 8 carbon atoms. Examples of cycloalkyl groups include cyclopentyl, cyclohexyl and isobornyl.

The term «alkoxy» means a group of formula —O-Alkyl.

The term «aryl» means an aromatic hydrocarbon group. A «C6-C12 aryl» means an aryl having 6 to 12 carbon atoms.

The term «heteroaryl» means an aromatic group comprising a heteroatom such as O, N, S and mixtures thereof. A «C5-C9 heteroaryl» means a heteroaryl having 5 to 9 carbon atoms.

The term «polyol» means a compound comprising at least two hydroxyl groups.

The term «polyester» means a compound comprising at least two ester bonds.

The term «polyether» means a compound comprising at least two ether bonds.

The term «polycarbonate» means a compound comprising at least two carbonate bonds.

The term «polyester polyol» means a polyester comprising at least two hydroxyl groups.

The term «polyether polyol» means a polyether comprising at least two hydroxyl groups.

The term «polycarbonate polyol» means a polycarbonate comprising at least two hydroxyl groups.

The term «hydrocarbon radical» means a radical consisting of carbon and hydrogen atoms. Unless mentioned otherwise a hydrocarbon radical is not substituted or interrupted by any heteroatoms (O, N or S). A hydrocarbon radical may be linear or branched, saturated or unsaturated, aliphatic, cycloaliphatic or aromatic.

The term «hydroxyl group» means a —OH group.

The term «amine» means a —$NR_aR_b$ group, wherein $R_a$ and $R_b$ are independently H or a C1-C6 alkyl. The term «primary amine» means a —$NH_2$ group. The term «secondary amine» means a —$NHR_a$ group wherein $R_a$ is a C1-C6 alkyl. The term «tertiary amine» means a —$NR_aR_b$ group, wherein $R_a$ and $R_b$ are independently a C1-C6 alkyl.

The term «carboxylic acid» means a —COOH group.

The term «isocyanate group» means a —N═C═O group.

The term «ester bond» means a —C(═O)—O— or —O—C(═O)— bond.

The term «ether bond» means a —O— bond.

The term «carbonate bond» means a —O—C(═O)—O— bond.

The term «urethane or carbamate» means a —NH—C(═O)—O— or —O—C(═O)—NH— bond.

The term «amide bond» means a —C(═O)—NH— or —NH—C(═O)— bond.

The term «urea bond» means a —NH—C(═O)—NH— bond.

The term «polyisocyanate» means a compound comprising at least two isocyanate groups.

The term «aliphatic» means a non-aromatic acyclic compound. It may be linear or branched, saturated or unsaturated. It may be substituted by one or more groups, for example selected from alkyl, hydroxyl, halogen (Br, Cl, I), isocyanate, carbonyl, amine, carboxylic acid, —C(═O)—OR', —C(═O)—O—C(═O)—R', each R' being independently a C1-C6 alkyl. It may comprise one or more bonds selected from ether, ester, amide, urethane, urea and mixtures thereof.

The term «alicyclic» means a compound that does not comprise any rings

The term «cycloaliphatic» means a non-aromatic cyclic compound. It may be substituted by one or more groups as defined for the term «aliphatic». It may comprise one or more bonds as defined for the term «aliphatic».

The term «aromatic» means a compound comprising an aromatic ring, which means that respects Hückel's aromaticity rule, in particular a compound comprising a phenyl group. It may be substituted by one or more groups as defined for the term «aliphatic». It may comprise one or more bonds as defined for the term «aliphatic».

The term «saturated» means a compound that does not comprise any double or triple carbon-carbon bonds.

The term «unsaturated» means a compound that comprises a double or triple carbon-carbon bond, in particular a double carbon-carbon bond.

The term «optionally substituted» means a compound substituted by one or more groups selected from alkyl, cycloalkyl, aryl, heteroaryl, alkoxy, alkylaryl, haloalkyl, hydroxyl, halogen, isocyanate, nitrile, amine, amide, carboxylic acid, —C(=O)—R'—C(=O)—OR', —C(=O) NH—R', —NH—C(=O)R', —O—C(=O)—NH—R', —NH—C(=O)—O—R', —C(=O)—O—C(=O)—R' and —SO$_2$—NH—R', each R' being independently an optionally substituted group selected from alkyl, aryl and alkylaryl.

The term «3D article» means a three-dimensional object obtained by 3D printing.

Ethylenically Unsaturated Compound a)

The composition of the invention comprises an ethylenically unsaturated compound a). The composition of the invention may comprise a mixture of ethylenically unsaturated compounds a).

As used herein, the term "ethylenically unsaturated compound" means a compound that comprises a polymerizable carbon-carbon double bond. A polymerizable carbon-carbon double bond is a carbon-carbon double bond that can react with another carbon-carbon double bond in a polymerization reaction. A polymerizable carbon-carbon double bond is generally comprised in a group selected from acrylate (including cyanoacrylate), methacrylate, acrylamide, methacrylamide, styrene, maleate, fumarate, itaconate, allyl, propenyl, vinyl and combinations thereof, preferably selected from acrylate, methacrylate and vinyl, more preferably selected from acrylate and methacrylate. The carbon-carbon double bonds of a phenyl ring are not considered as polymerizable carbon-carbon double bonds.

In one embodiment, the ethylenically unsaturated compound a) may be selected from one or more (meth)acrylate-functionalized monomers, one or more (meth)acrylate-functionalized oligomers and mixtures thereof.

As used herein, the term "(meth)acrylate-functionalized monomer" means a monomer comprising a (meth)acrylate group, in particular an acrylate group. The term "(meth)acrylate-functionalized oligomer" means an oligomer comprising a (meth)acrylate group, in particular an acrylate group. The term "(meth)acrylate group" encompasses acrylate groups (—O—CO—CH=CH$_2$) and methacrylate groups (—O—CO—C(CH$_3$)=CH$_2$).

Preferably, the (meth)acrylate-functionalized monomer and/or the (meth)acrylate-functionalized oligomer do not comprise any amino group.

As used herein, the term "amino group" refers to a primary, secondary or tertiary amine group, but does not include any other type of nitrogen-containing group such as an amide, carbamate (urethane), urea, or sulfonamide group).

In one embodiment, the ethylenically unsaturated compound comprises a (meth)acrylate-functionalized monomer. The ethylenically unsaturated compound may comprise a mixture of (meth)acrylate-functionalized monomers.

The (meth)acrylate-functionalized monomer may have a molecular weight of less than 600 g/mol, in particular from 100 to 550 g/mol, more particularly 200 to 500 g/mol.

The (meth)acrylate-functionalized monomer may have 1 to 6 (meth)acrylate groups, in particular 1 to 5 (meth)acrylate groups, more particularly 1 to 3 (meth)acrylate groups.

The (meth)acrylate-functionalized monomer may comprise a mixture of (meth)acrylate-functionalized monomers having different functionalities. For example the (meth)acrylate-functionalized monomer may comprise a mixture of a (meth)acrylate-functionalized monomer containing a single acrylate or methacrylate group per molecule (referred to herein as "mono(meth)acrylate-functionalized compounds") and a (meth)acrylate-functionalized monomer containing 2 or more, preferably 2 or 3, acrylate and/or methacrylate groups per molecule. In another example, the (meth)acrylate-functionalized monomer may comprise a mixture of at least one mono(meth)acrylate-functionalized compound and at least one (meth)acrylate-functionalized monomer containing 3 or more, preferably 4 or more, (meth)acrylate groups per molecule.

The (meth)acrylate functionalized monomer may comprise a mono(meth)acrylate-functionalized monomer. The mono(meth)acrylate-functionalized monomer may advantageously function as a reactive diluent and reduce the viscosity of the composition of the invention.

Examples of suitable mono(meth)acrylate-functionalized monomers include, but are not limited to, mono-(meth)acrylate esters of aliphatic alcohols (wherein the aliphatic alcohol may be straight chain, branched or alicyclic and may be a mono-alcohol, a di-alcohol or a polyalcohol, provided only one hydroxyl group is esterified with (meth)acrylic acid); mono-(meth)acrylate esters of aromatic alcohols (such as phenols, including alkylated phenols); mono-(meth)acrylate esters of alkylaryl alcohols (such as benzyl alcohol); mono-(meth)acrylate esters of oligomeric and polymeric glycols such as diethylene glycol, triethylene glycol, dipropylene glycol, tripropylene glycol, polyethylene glycol, and polypropylene glycol); mono-(meth)acrylate esters of monoalkyl ethers of glycols and oligoglycols; mono-(meth)acrylate esters of alkoxylated (e.g., ethoxylated and/or propoxylated) aliphatic alcohols (wherein the aliphatic alcohol may be straight chain, branched or alicyclic and may be a mono-alcohol, a di-alcohol or a polyalcohol, provided only one hydroxyl group of the alkoxylated aliphatic alcohol is esterified with (meth)acrylic acid); mono-(meth)acrylate esters of alkoxylated (e.g., ethoxylated and/or propoxylated) aromatic alcohols (such as alkoxylated phenols); caprolactone mono(meth)acrylates; and the like.

The following compounds are specific examples of mono (meth)acrylate-functionalized monomers suitable for use in the curable compositions of the present invention: methyl (meth)acrylate; ethyl (meth)acrylate; n-propyl (meth)acrylate; n-butyl (meth)acrylate; isobutyl (meth)acrylate; n-hexyl (meth)acrylate; 2-ethylhexyl (meth)acrylate; n-octyl (meth)acrylate; isooctyl (meth)acrylate; n-decyl (meth)acrylate; n-dodecyl (meth)acrylate; tridecyl (meth)acrylate; tetradecyl (meth)acrylate; hexadecyl (meth)acrylate; 2-hydroxyethyl (meth)acrylate; 2- and 3-hydroxypropyl (meth) acrylate; 2-methoxyethyl (meth)acrylate; 2-ethoxyethyl (meth)acrylate; 2- and 3-ethoxypropyl (meth)acrylate; tetrahydrofurfuryl (meth)acrylate; alkoxylated tetrahydrofurfuryl (meth)acrylate; 2-(2-ethoxyethoxy)ethyl (meth)acrylate; cyclohexyl (meth)acrylate; glycidyl (meth)acrylate; isodecyl (meth)acrylate; lauryl (meth)acrylate; 2-phenoxyethyl (meth)acrylate; alkoxylated phenol (meth)acrylates; alkoxylated nonylphenol (meth)acrylates; cyclic trimethylolpropane formal (meth)acrylate; isobornyl (meth)acrylate; tricyclodecanemethanol (meth)acrylate; tert-butylcyclohexanol (meth)acrylate; trimethylcyclohexanol (meth)acrylate; diethylene glycol monomethyl ether (meth)acrylate; diethylene glycol monoethyl ether (meth)acrylate; diethylene glycol monobutyl ether (meth)acrylate; triethylene glycol monoethyl ether (meth)acrylate; ethoxylated lauryl (meth)acrylate; methoxy polyethylene glycol (meth)acrylates; hydroxyl ethyl-butyl urethane (meth)acrylates; 3-(2-hydroxyalkyl)oxazolidinone (meth)acrylates; and combinations thereof.

The (meth)acrylate functionalized monomer may comprise a (meth)acrylate-functionalized monomer containing two or more (meth)acrylate groups per molecule.

Examples of suitable (meth)acrylate-functionalized monomers containing two or more (meth)acrylate groups per molecule include acrylate and methacrylate esters of polyhydric alcohols (organic compounds containing two or more, e.g., 2 to 6, hydroxyl groups per molecule). Specific examples of suitable polyhydric alcohols include $C_{2-20}$ alkylene glycols (glycols having a $C_{2-10}$ alkylene group may be preferred, in which the carbon chain may be branched; e.g., ethylene glycol, trimethylene glycol, 1,2-propylene glycol, 1,2-butanediol, 1,3-butanediol, 2,3-butanediol, tetramethylene glycol (1,4-butanediol), 1,5-pentanediol, 1,6-hexanediol, 1,8-octanediol, 1,9-nonanediol, 1,12-dodecanediol, cyclohexane-1,4-dimethanol, bisphenols, and hydrogenated bisphenols, as well as alkoxylated (e.g., ethoxylated and/or propoxylated) derivatives thereof), diethylene glycol, glycerin, alkoxylated glycerin, triethylene glycol, dipropylene glycol, tripropylene glycol, trimethylolpropane, alkoxylated trimethylolpropane, ditrimethylolpropane, alkoxylated ditrimethylolpropane, pentaerythritol, alkoxylated pentaerythritol, dipentaerythritol, alkoxylated dipentaerythritol, cyclohexanediol, alkoxylated cyclohexanediol, cyclohexanedimethanol, alkoxylated cyclohexanedimethanol, norbornene dimethanol, alkoxylated norbornene dimethanol, norbornane dimethanol, alkoxylated norbornane dimethanol, polyols containing an aromatic ring, cyclohexane-1,4-dimethanol ethylene oxide adducts, bis-phenol ethylene oxide adducts, hydrogenated bisphenol ethylene oxide adducts, bisphenol propylene oxide adducts, hydrogenated bisphenol propylene oxide adducts, cyclohexane-1,4-dimethanol propylene oxide adducts, sugar alcohols and alkoxylated sugar alcohols. Such polyhydric alcohols may be fully or partially esterified (with (meth)acrylic acid, (meth)acrylic anhydride, (meth)acryloyl chloride or the like), provided they contain at least two (meth)acrylate functional groups per molecule. As used herein, the term "alkoxylated" refers to compounds containing one or more oxyalkylene moieties (e.g., oxyethylene and/or oxypropylene moieties). An oxyalkylene moiety corresponds to the general structure —R—O—, wherein R is a divalent aliphatic moiety such as —$CH_2CH_2$— or —$CH_2CH(CH_3)$—. For example, an alkoxylated compound may contain from 1 to 30 oxyalkylene moieties per molecule.

Exemplary (meth)acrylate-functionalized monomers containing two or more (meth)acrylate groups per molecule may include ethoxylated bisphenol A di(meth)acrylates; triethylene glycol di(meth)acrylate; ethylene glycol di(meth)acrylate; tetraethylene glycol di(meth)acrylate; polyethylene glycol di(meth)acrylates; 1,4-butanediol diacrylate; 1,4-butanediol dimethacrylate; diethylene glycol diacrylate; diethylene glycol dimethacrylate, 1,6-hexanediol diacrylate; 1,6-hexanediol dimethacrylate; neopentyl glycol diacrylate; neopentyl glycol di(meth)acrylate; polyethylene glycol (600) dimethacrylate (where 600 refers to the approximate number average molecular weight of the polyethylene glycol portion); polyethylene glycol (200) diacrylate; 1,12-dodecanediol dimethacrylate; tetraethylene glycol diacrylate; triethylene glycol diacrylate, 1,3-butylene glycol dimethacrylate, tripropylene glycol diacrylate, polybutadiene diacrylate; methyl pentanediol diacrylate; polyethylene glycol (400) diacrylate; ethoxylated$_2$ bisphenol A dimethacrylate; ethoxylated$_3$ bisphenol A dimethacrylate; ethoxylated$_3$ bisphenol A diacrylate; cyclohexane dimethanol dimethacrylate; cyclohexane dimethanol diacrylate; ethoxylated$_{10}$ bisphenol A dimethacrylate (where the numeral following "ethoxylated" is the average number of oxyalkylene moieties per molecule); dipropylene glycol diacrylate; ethoxylated$_4$ bisphenol A dimethacrylate; ethoxylated$_6$ bisphenol A dimethacrylate; ethoxylated$_8$ bisphenol A dimethacrylate; alkoxylated hexanediol diacrylates; alkoxylated cyclohexane dimethanol diacrylate; dodecane diacrylate; ethoxylated$_4$ bisphenol A diacrylate; ethoxylated$_{10}$ bisphenol A diacrylate; polyethylene glycol (400) dimethacrylate; polypropylene glycol (400) dimethacrylate; metallic diacrylates; modified metallic diacrylates; metallic dimethacrylates; polyethylene glycol (1000) dimethacrylate; methacrylated polybutadiene; propoxylated$_2$ neopentyl glycol diacrylate; ethoxylated$_{30}$ bisphenol A dimethacrylate; ethoxylated$_{30}$ bisphenol A diacrylate; alkoxylated neopentyl glycol diacrylates; polyethylene glycol dimethacrylates; 1,3-butylene glycol diacrylate; ethoxylated$_2$ bisphenol A dimethacrylate; dipropylene glycol diacrylate; ethoxylated$_4$ bisphenol A diacrylate; polyethylene glycol (600) diacrylate; polyethylene glycol (1000) dimethacrylate; tricyclodecane dimethanol diacrylate; propoxylated neopentyl glycol diacrylates such as propoxylated$_2$ neopentyl glycol diacrylate; diacrylates of alkoxylated aliphatic alcohols; trimethylolpropane trimethacrylate; trimethylolpropane triacrylate; tris (2-hydroxyethyl) isocyanurate triacrylate; ethoxylated$_{20}$ trimethylolpropane triacrylate; pentaerythritol triacrylate; ethoxylated$_3$ trimethylolpropane triacrylate; propoxylated$_3$ trimethylolpropane triacrylate; ethoxylated$_6$ trimethylolpropane triacrylate; propoxylated$_6$ trimethylolpropane triacrylate; ethoxylated$_9$ trimethylolpropane triacrylate; alkoxylated trifunctional acrylate esters; trifunctional methacrylate esters; trifunctional acrylate esters; propoxylated$_3$ glyceryl triacrylate; propoxylated$_{5.5}$ glyceryl triacrylate; ethoxylated$_{15}$ trimethylolpropane triacrylate; trifunctional phosphoric acid esters; trifunctional acrylic acid esters; pentaerythritol tetraacrylate; di-trimethylolpropane tetraacrylate; ethoxylated$_4$ pentaerythritol tetraacrylate; pentaerythritol polyoxyethylene tetraacrylate; dipentaerythritol pentaacrylate; and pentaacrylate esters.

The curable composition of the invention may comprise 10 to 80%, in particular 15 to 75%, more particularly 20 to 70%, by weight of (meth)acrylate-functionalized monomer based on the total weight of the curable composition.

In one embodiment, the ethylenically unsaturated compound comprises a (meth)acrylate-functionalized oligomer. The ethylenically unsaturated compound may comprise a mixture of (meth)acrylate-functionalized oligomers.

The (meth)acrylate-functionalized oligomer may be selected in order to enhance the flexibility, strength and/or modulus, among other attributes, of a cured polymer prepared using the curable composition of the present invention.

The (meth)acrylate functionalized oligomer may have 1 to 18 (meth)acrylate groups, in particular 2 to 6 (meth)acrylate groups, more particularly 2 to 6 acrylate groups.

The (meth)acrylate functionalized oligomer may have a number average molecular weight equal or more than 600 g/mol, in particular 800 to 15,000 g/mol, more particularly 1,000 to 5,000 g/mol.

In particular, the (meth)acrylate-functionalized oligomers may be selected from the group consisting of (meth)acrylate-functionalized urethane oligomers (sometimes also referred to as "urethane (meth)acrylate oligomers," "polyurethane (meth)acrylate oligomers" or "carbamate (meth)acrylate oligomers"), (meth)acrylate-functionalized epoxy oligomers (sometimes also referred to as "epoxy (meth)acrylate oligomers"), (meth)acrylate-functionalized polyether oligomers (sometimes also referred to as "polyether (meth)acrylate oligomers"), (meth)acrylate-functionalized polydiene oligomers (sometimes also referred to as "polydiene (meth)acrylate oligomers"), (meth)acrylate-functionalized polycarbonate oligomers (sometimes also referred to as "polycarbonate (meth)acrylate oligomers"), and (meth)acrylate-functionalized polyester oligomers (sometimes also referred to as "polyester (meth)acrylate oligomers") and mixtures thereof.

Preferably, the (meth)acrylate-functionalized oligomer comprises a (meth)acrylate-functionalized urethane oligomer, more preferably an acrylate-functionalized urethane oligomer.

Advantageously, the (meth)acrylate-functionalized oligomer comprises a (meth)acrylate-functionalized urethane oligomer having two (meth)acrylate groups, more preferably an acrylate-functionalized urethane oligomer having two acrylate groups.

Exemplary polyester (meth)acrylate oligomers include the reaction products of acrylic or methacrylic acid or mixtures or synthetic equivalents thereof with hydroxyl group-terminated polyester polyols. The reaction process may be conducted such that all or essentially all of the hydroxyl groups of the polyester polyol have been (meth)acrylated, particularly in cases where the polyester polyol is difunctional. The polyester polyols can be made by polycondensation reactions of polyhydroxyl functional components (in particular, diols) and polycarboxylic acid functional compounds (in particular, dicarboxylic acids and anhydrides). The polyhydroxyl functional and polycarboxylic acid functional components can each have linear, branched, cycloaliphatic or aromatic structures and can be used individually or as mixtures.

Examples of suitable epoxy (meth)acrylates include the reaction products of acrylic or methacrylic acid or mixtures thereof with an epoxy resin (polyglycidyl ether or ester). The epoxy resin may, in particular, by selected from bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxycyclohexanecarboxylate, 2-(3,4-epoxycyclohexyl-5,5-spiro-3,4-epoxy) cyclohexane-1,4-dioxane, bis(3,4-epoxycyclohexylmethyl) adipate, vinylcyclohexene oxide, 4-vinylepoxycyclohexane, bis(3,4-epoxy-6-methylcyclohexylmethyl)adipate,3,4-epoxy-6-methylcyclohexy I-3',4'-epoxy-6'-methylcyclohexanecarboxylate, methylenebis(3,4-epoxycyclohexane), dicyclopentadiene diepoxide, di(3,4-epoxycyclohexylmethyl) ether of ethylene glycol, ethylenebis(3,4-epoxycyclohexanecarboxylate), 1,4-butanediol diglycidyl ether, 1,6-hexanediol diglycidyl ether, glycerol triglycidyl ether, trimethylolpropane triglycidyl ether, polyethylene glycol diglycidyl ether, polypropylene glycol diglycidyl ether, polyglycidyl ethers of a polyether polyol obtained by the addition of one or more alkylene oxides to an aliphatic polyhydric alcohol such as ethylene glycol, propylene glycol, and glycerol, diglycidyl esters of aliphatic long-chain dibasic acids, monoglycidyl ethers of aliphatic higher alcohols, monoglycidyl ethers of phenol, cresol, butyl phenol, or polyether alcohols obtained by the addition of alkylene oxide to these compounds, glycidyl esters of higher fatty acids, epoxidized soybean oil, epoxybutylstearic acid, epoxyoctylstearic acid, epoxidized linseed oil, epoxidized polybutadiene, and the like.

Suitable polyether (meth)acrylate oligomers include, but are not limited to, the condensation reaction products of acrylic or methacrylic acid or synthetic equivalents or mixtures thereof with polyetherols which are polyether polyols (such as polyethylene glycol, polypropylene glycol or polytetramethylene glycol). Suitable polyetherols can be linear or branched substances containing ether bonds and terminal hydroxyl groups. Polyetherols can be prepared by ring opening polymerization of cyclic ethers such as tetrahydrofuran or alkylene oxides (e.g., ethylene oxide and/or propylene oxide) with a starter molecule. Suitable starter molecules include water, polyhydroxyl functional materials, polyester polyols and amines.

Polyurethane (meth)acrylate oligomers (sometimes also referred to as "urethane (meth)acrylate oligomers") suitable for use in the curable compositions of the present invention include urethanes based on aliphatic, cycloaliphatic and/or aromatic polyester polyols and polyether polyols and aliphatic, cycloalipahtic and/or aromatic polyester diisocyanates and polyether diisocyanates capped with (meth)acrylate end-groups. Suitable polyurethane (meth)acrylate oligomers include, for example, aliphatic polyester-based urethane di- and tetra-acrylate oligomers, aliphatic polyether-based urethane di- and tetra-acrylate oligomers, as well as aliphatic polyester/polyether-based urethane di- and tetra-acrylate oligomers.

The polyurethane (meth)acrylate oligomers may be prepared by reacting aliphatic, cycloaliphatic and/or aromatic polyisocyanates (e.g., diisocyanate, triisocyanate) with OH group terminated polyester polyols, polyether polyols, polycarbonate polyols, polycaprolactone polyols, polyorganosiloxane polyols (e.g., polydimethylsiloxane polyols), or polydiene polyols (e.g., polybutadiene polyols), or combinations thereof to form isocyanate-functionalized oligomers which are then reacted with hydroxyl-functionalized (meth)acrylates such as hydroxyethyl acrylate or hydroxyethyl methacrylate to provide terminal (meth)acrylate groups. For example, the polyurethane (meth)acrylate oligomers may contain two, three, four or more (meth)acrylate functional groups per molecule. Other orders of addition may also be practiced to prepare the polyurethane (meth)acrylate, as is known in the art. For example, the hydroxyl-functionalized (meth)acrylate may be first reacted with a polyisocyanate to obtain an isocyanate-functionalized (meth)acrylate, which may then be reacted with an OH group terminated polyester polyol, polyether polyol, polycarbonate polyol, polycaprolactone polyol, polydimethysiloxane polyol, polybutadiene polyol, or a combination thereof. In yet another embodiment, a polyisocyanate may be first reacted with a polyol, including any of the aforementioned types of polyols, to obtain an isocyanate-functionalized polyol, which is thereafter reacted with a hydroxyl-functionalized (meth)acrylate to yield a polyurethane (meth)acrylate. Alternatively, all the components may be combined and reacted at the same time.

Suitable acrylic (meth)acrylate oligomers (sometimes also referred to in the art as "acrylic oligomers") include oligomers which may be described as substances having an oligomeric acrylic backbone which is functionalized with one or (meth)acrylate groups (which may be at a terminus of the oligomer or pendant to the acrylic backbone). The acrylic backbone may be a homopolymer, random copolymer or block copolymer comprised of repeating units of acrylic monomers. The acrylic monomers may be any monomeric (meth)acrylate such as C1-C6 alkyl (meth)acrylates as well as functionalized (meth)acrylates such as (meth)acrylates bearing hydroxyl, carboxylic acid and/or epoxy groups.

Acrylic (meth)acrylate oligomers may be prepared using any procedures known in the art, such as by oligomerizing monomers, at least a portion of which are functionalized with hydroxyl, carboxylic acid and/or epoxy groups (e.g., hydroxyalkyl(meth)acrylates, (meth)acrylic acid, glycidyl (meth)acrylate) to obtain a functionalized oligomer intermediate, which is then reacted with one or more (meth)acrylate-containing reactants to introduce the desired (meth)acrylate functional groups.

The curable composition of the invention may comprise 10 to 80%, in particular 15 to 75%, more particularly 20 to 70%, by weight of (meth)acrylate-functionalized oligomer based on the total weight of the curable composition.

In a first embodiment, the ethylenically unsaturated compound a) consists essentially of one or more (meth)acrylate-functionalized monomers as defined above and optionally one or more (meth)acrylate-functionalized oligomers as defined above.

In a second embodiment, the ethylenically unsaturated compound a) consists essentially of a mixture of one or more (meth)acrylate-functionalized monomers as defined above and one or more (meth)acrylate-functionalized oligomers as defined above.

In a third embodiment, the ethylenically unsaturated compound a) consists essentially of one or more (meth)acrylate-functionalized oligomers as defined above and optionally one or more (meth)acrylate-functionalized monomers as defined above.

Photoinitiator b)

The composition of the invention comprises a phosphine oxide photoinitiator b) having both Norrish Type I and Norrish type II activity. The composition of the invention may comprise a mixture of phosphine oxide photoinitiators b).

As used herein, the term "phosphine oxide" refers to a compound comprising a —P(=O)— group. Photoinitiators are generally divided into two classes, depending on their mode of action: radical photoinitiators and cationic photoinitiators. Cationic Photoinitiators are often salts, for instance iodonium and sulfonium salts. When these salts are irradiated with UV-light, they undergo homolytic bond cleavage forming radicals that react with a proton donor to give a Brønsted or Lewis acid. The generated acid then initiates the polymerization. Radical photoinitiators can adopt two different modes of action, and are classified by mode of action as Norrish Type I and Norrish Type II photoinitiators.

As used herein, the term "activity" with reference to Norrish Type I and Norrish Type II activity is intended to relate to Norrish photoinitiation and analogous reactions. For instance, a photoinitiator having Norrish Type I activity within the scope of this invention would be a photoinitiator characterized by a cleavage reaction into two radical fragments of the original photoinitiator on exposure to UV light. For an initiator having Norrish Type II activity, exposure to UV light causes the abstraction of an atom, such as hydrogen, to generate the radical.

The phosphine oxide photoinitiator b) used in the composition of the invention comprises two photoactive units. The first photoactive unit may have a Norrish Type I activity and be cleaved into two radical fragments on exposure to UV light. The second photoactive unit may have a Norrish Type II activity and be transformed into a radical by abstraction of an atom (i.e. a hydrogen atom) on exposure to UV light.

For example, the phosphine oxide photoinitiator b) may have a first phosphine oxide photoactive unit of formula —P(=O)—C(=O)—, preferably a first acyl phosphine oxide photoactive unit of formula —P(=O)—C(=O)—Ar$_1$—, and a second aromatic ketone photoactive unit of formula —C(=O)—Ar$_2$ which is distinct from the first photoactive unit, wherein Ar$_1$ and Ar$_2$ are independently an optionally substituted aryl, preferably an optionally substituted phenyl. In a preferred embodiment, the second aromatic ketone photoactive unit may be covalently bound (i.e. with a direct bond) to the aryl group of the first acyl phosphine oxide photoactive unit, in particular forming a moiety of formula —P(=O)—C(=O)—Ar$_1$—C(=O)—Ar$_2$—. This advantageously leads to the presence of two photoactive units having different photo-absorption wavelengths in the same molecule. In the aromatic ketone photoactive unit, the photoactivity is through a so-called Type 2 mechanism, that of proton abstraction from a suitable synergist such as a tertiary amine. This gives rise to a process of radical formation which is much less sensitive to oxygen inhibition than the radical forming process in the phosphine oxide photoactive unit which is a Type 1 mechanism involving free radicals generated by the scission of the (OP)—(C=O) bond.

In one embodiment, the phosphine oxide photoinitiator b) has the following formula (I):

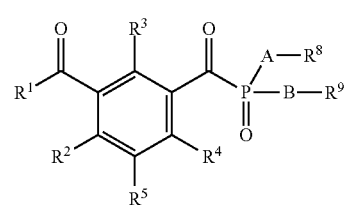

(I)

wherein

R$^1$ is C$_{1-20}$ alkyl, C$_7$-C$_{20}$ alkylaryl or an optionally substituted phenyl or polyphenyl;

R$^2$, R$^3$, R$^4$ and R$^5$ are independently hydrogen, halogen, C$_{1-20}$ alkyl, —OR$^6$ or CF$_3$ and two of radicals R$^2$, R$^3$, R$^4$ and R$^5$ may together form C$_{1-20}$ alkylene which can be interrupted by O, S or NR$^7$;

R$^6$ is hydrogen, C$_{1-20}$ alkyl, C$_{2-20}$ alkenyl, C$_3$-C$_8$ cycloalkyl, phenyl, benzyl or C$_{2-20}$ alkyl which is interrupted once or more than once by O or S and which is unsubstituted or is substituted by OH and/or SH;

R$^7$ is hydrogen, phenyl, C$_{1-12}$ alkyl or C$_{2-12}$ alkyl which is interrupted once or more than once by O or S and which is unsubstituted or substituted by OH and/or SH;

R$^8$ and R$^9$ are independently an optionally substituted group selected from C$_1$-C$_{20}$ alkyl, C$_1$-C$_{20}$ alkoxy, C$_{2-20}$ alkenyl, C$_3$-C$_8$ cycloalkyl, C$_6$-C$_{12}$ aryl, C$_7$-C$_{20}$ alkylaryl and C$_5$-C$_9$ heteroaryl;

A and B are independently a bond, —(CH$_2$)$_n$— or —C(=O)—;

n is 1 to 10.

In particular, R$^1$ may be C$_{1-12}$ alkyl, benzyl or an optionally substituted phenyl. More particularly, R$^1$ may be phenyl.

In particular, R$^2$, R$^3$ and R$^4$ may independently be hydrogen, halogen, C$_{1-12}$ alkyl or C$_1$-C$_{12}$ alkoxy. More particularly, R$^2$, R$^3$ and R$^4$ may independently be hydrogen, Cl, methyl or methoxy. Even more particularly, R$^2$, R$^3$ and R$^4$ may be methyl.

In particular, R$^5$ may be hydrogen.

In particular, R$^8$ and R$^9$ may independently be C$_1$-C$_{12}$ alkyl, C$_1$-C$_{12}$ alkoxy or an optionally substituted phenyl.

In particular A and B may independently be a bond or —C(=O)—.

More particularly, -A-R$^8$ and —B—R$^9$ may independently be phenyl, methoxy, ethoxy, trimethylpentyl or a group of formula (II):

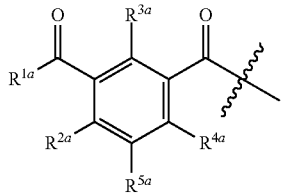

(II)

wherein

R$^{1a}$, R$^{2a}$, R$^{3a}$, R$^{4a}$ and R$^{5a}$ are respectively as defined above for R$^1$, R$^2$, R$^3$, R$^4$ and R$^5$.

Even more particularly, -A-R$^8$ is phenyl and —B—R$^9$ is phenyl, methoxy, ethoxy, trimethylpentyl or a group of formula (II) as defined above.

In a preferred embodiment, the phosphine oxide photoinitiator b) is according to formula (I), wherein R$^1$ is C$_{1-12}$ alkyl, benzyl or an optionally substituted phenyl;

R$^2$, R$^3$ and R$^4$ are independently hydrogen, halogen, C$_{1-12}$ alkyl or C$_1$-C$_{12}$ alkoxy;

R$^5$ is hydrogen;

R$^8$ and R$^9$ are independently C$_1$-C$_{12}$ alkyl, C$_1$-C$_{12}$ alkoxy or an optionally substituted phenyl;

A and B are independently a bond or —C(=O)—.

In a particularly preferred embodiment, the phosphine oxide photoinitiator b) is according to formula (I), wherein R$^1$ is phenyl;

R$^2$, R$^3$ and R$^4$ are independently hydrogen, Cl, methyl or methoxy; preferably methyl;

R$^5$ is hydrogen;

-A-R$^8$ and —B—R$^9$ are independently phenyl, methoxy, ethoxy, trimethylpentyl or a group of formula (II) as defined above; preferably -A-R$^8$ is phenyl and —B—R$^9$ is phenyl, methoxy, ethoxy, trimethylpentyl or a group of formula (II) as defined above.

The phosphine oxide photoinitiator b) may, in particular, be selected from the following compounds:

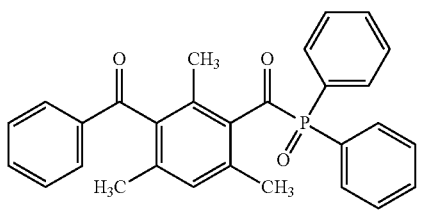

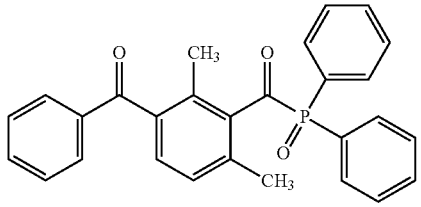

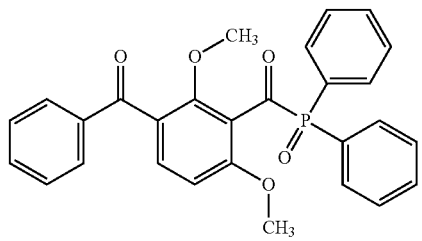

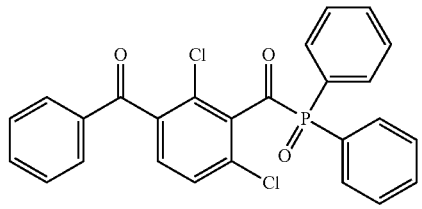

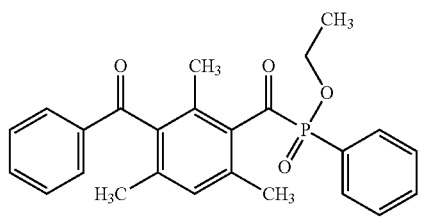

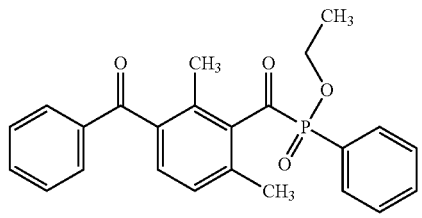

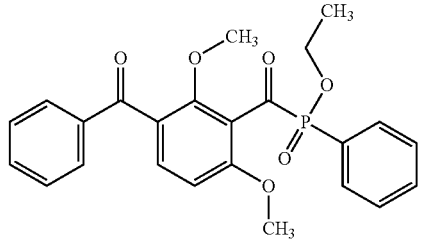

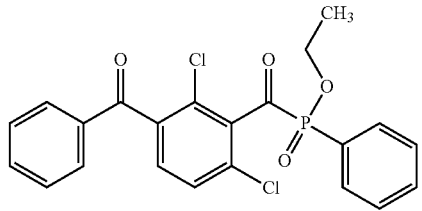

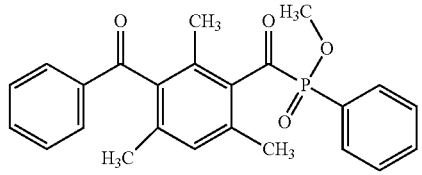

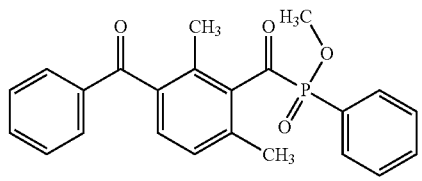

-continued

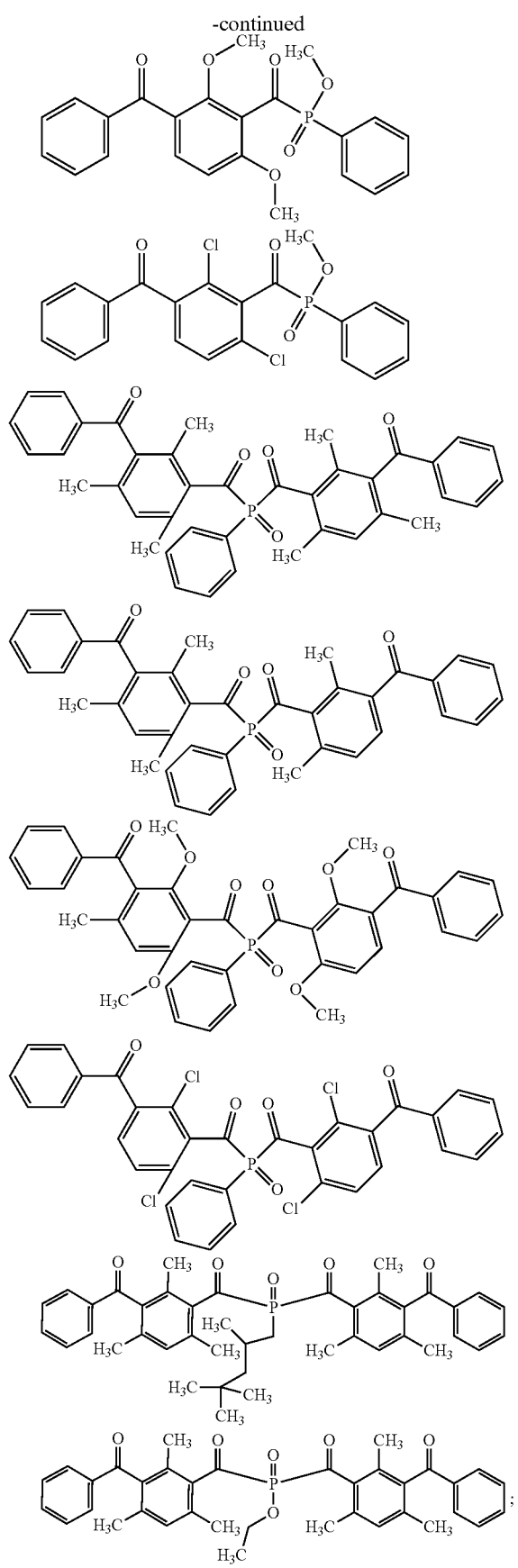

and mixtures thereof.

Particularly preferred compounds are selected from

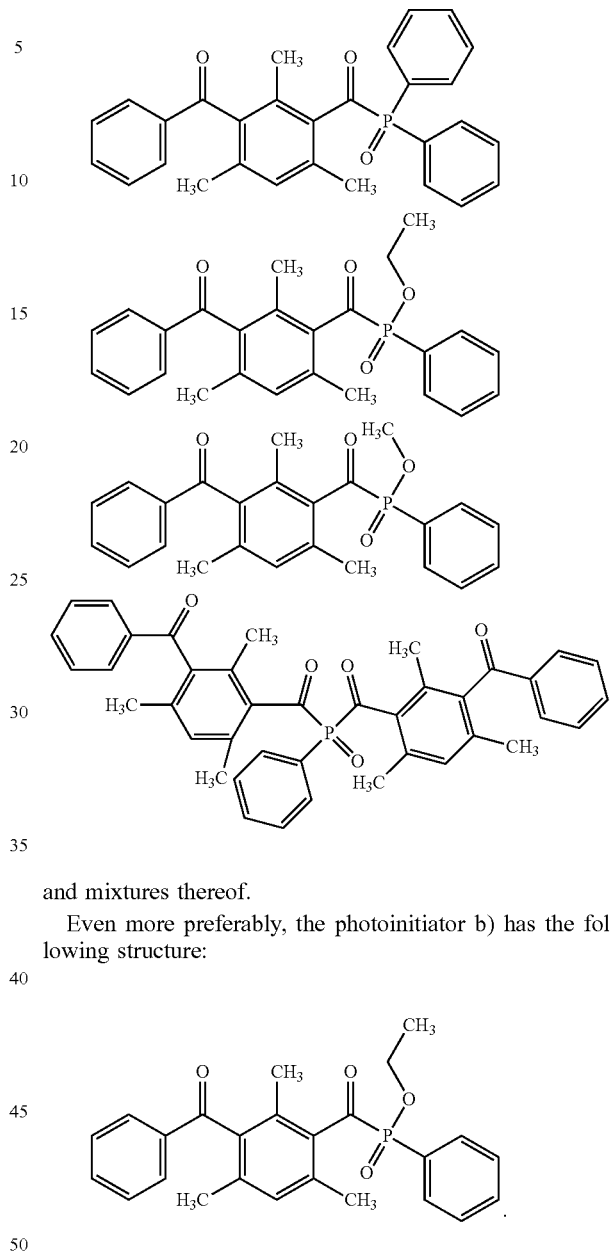

and mixtures thereof.

Even more preferably, the photoinitiator b) has the following structure:

The curable composition of the invention may comprise 0.05% to 10%, in particular 0.1% to 5%, more particularly 0.5 to 2%, by weight of phosphine oxide photoinitiator b) based on the total weight of the curable composition. For example, the amount of phosphine oxide photoinitiator b) may be from 0.05 to 5%, from 0.1 to 4%, from 0.2 to 3%, from 0.3 to 2.5% or from 0.4 to 2% based on the total weight of the curable composition. Alternatively, the amount of phosphine oxide photoinitiator b) may be from 2 to 8%, from 2.5 to 7%, from 2.5 to 6%, from 2.5 to 5.5% or from 3 to 5% based on the total weight of the curable composition.

Cationically Polymerizable Compound

The composition of the invention may further comprise a cationically polymerizable compound. The composition of the invention may comprise a mixture of cationically polymerizable compounds.

When the composition comprises a cationically polymerizable compound, the composition may be a hybrid free-radical/cationic composition, i.e. a composition that is cure by free radical polymerization and cationic polymerization.

The term "cationically polymerizable compound" means a compound comprising a polymerizing functional group which polymerizes via a cationic mechanism, for example a heterocyclic group or a carbon-carbon double bond substituted with an electrodonating group. In a cationic polymerization mechanism, a cationic initiator transfers charge to the cationically polymerizable compound which then becomes reactive and leads to chain growth by reaction with another cationically polymerizable compound.

The cationically polymerizable compound may be selected from epoxy-functionalized compounds, oxetanes, oxolanes, cyclic acetals, cyclic lactones, thiiranes, thiethanes, spiro orthoesters, ethylenically unsaturated compounds other than (meth)acrylates, derivatives thereof and mixtures thereof.

In a preferred embodiment, the cationically polymerizable compound may be selected from epoxy-functionalized compounds, oxetanes and mixtures thereof, in particular aromatic epoxy-functionalized compounds, cycloaliphatic epoxy-functionalized compounds, oxetanes and mixtures thereof.

Suitable epoxy-functionalized compounds capable of being cationically polymerized are glycidyl ethers, in particular mono-, di-, tri- and polyglycidyl ether compounds, and alicyclic ether compounds including those comprising residue of carboxylic acids such as, for example, alkylcarboxylic acid residual groups, alkylcycloalkylcarboxylic acid residual groups and dialkyl dicarboxylic acid residual groups. For example, the epoxy-functionalized compounds may be bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxy-cyclohexanecarboxylate, 2-(3,4-epoxycyclohexyl-5,5-spiro-3,4-epoxy)cyclohexane-1,4-dioxane, bis(3,4-epoxycyclohexylmethyl)adipate, vinylcyclohexene oxide, 4-vinylepoxycyclohexane, bis(3,4-epoxy-6-methylcyclohexylmethyl)adipate, 3,4-epoxy-6-methylcyclohexyl-3',4'-epoxy-6'-methylcyclohexanecarboxylate, methylenebis(3,4-epoxycyclohexane), dicyclopentadiene diepoxide, di(3,4-epoxycyclohexylmethyl) ether of ethylene glycol, ethylenebis(3,4-epoxycyclohexanecarboxylate), epoxy-hexahydrodioctylphthalate, epoxyhexahydro-di-2-ethyl-hexyl phthalate, 1,4-butanediol diglycidyl ether, 1,6-hexanediol diglycidyl ether, glycerol triglycidyl ether, trimethylolpropane triglycidyl ether, polyethylene glycol diglycidyl ether, polypropylene glycol diglycidyl ether, polyglycidyl ethers of polyether polyol obtained by the addition of one or more alkylene oxides to aliphatic polyhydric alcohols such as ethylene glycol, propylene glycol, and glycerol, diglycidyl esters of aliphatic long-chain dibasic acids, monoglycidyl ethers of aliphatic higher alcohols, monoglycidyl ethers of phenol, cresol, butyl phenol, or polyether alcohols obtained by the addition of alkylene oxide to these compounds, glycidyl esters of higher fatty acids, epoxidized soybean oil, epoxybutylstearic acid, epoxyoctylstearic acid, epoxidized linseed oil, epoxidized polybutadiene, and the like.

Suitable oxetanes capable of being cationically polymerized include trimethylene oxide, 3,3-dimethyloxetane, 3,3-dichloromethyloxetane, 3-ethyl-3-phenoxymethyloxetane, and bis(3-ethyl-3-methyloxy)butane, 3-ethyl-3-oxetanemethanol.

Suitable oxolanes capable of being cationically polymerized include tetrahydrofuran and 2,3-dimethyltetrahydrofuran.

Suitable cyclic acetals capable of being cationically polymerized include trioxane, 1,3-dioxolane, and 1,3,6-trioxanecyclooctane.

Suitable cyclic lactones capable of being cationically polymerized include β-propiolactone and ε-caprolactone.

Suitable thiiranes capable of being cationically polymerized include ethylene sulfide, 1,2-propylene sulfide, and thioepichlorohydrin.

Suitable thiethanes capable of being cationically polymerized include 3,3-dimethylthiethane.

Suitable spiro orthoesters capable of being cationically polymerized are compounds obtained by the reaction of an epoxy compound and a lactone.

Suitable ethylenically unsaturated compounds other than (meth)acrylates capable of being cationically polymerized include vinyl ethers such as ethylene glycol divinyl ether, triethylene glycol divinyl ether and trimethylolpropane trivinyl ether; aliphatic vinyl monomers such as vinylcyclohexane; olefins such as isobutylene; dienes such as butadiene; vinyl alkyl ethers; vinyl aromatic monomers such as styrene and alkylstyrenes; unsaturated polymers such as polybutadiene; derivatives of the above organic substances; and the like, at least some of which may also be polymerizable by free radical mechanisms.

When the composition of the invention comprises a cationically polymerizable compound, it may further comprise a polyol. Suitable polyols are as defined above.

The curable composition of the invention may comprise 10 to 80%, in particular 15 to 75%, more particularly 20 to 70%, by weight of cationically polymerizable compound based on the total weight of the curable composition.

Other Photoinitiator

The curable composition of the invention may further comprise a photoinitiator other than b). The composition may comprise a mixture of photoinitiators other than b).

The photoinitiator other than b) may be a selected from a radical photoinitiator, a cationic photoinitiator and mixtures thereof.

In one embodiment, the photoinitiator other than b) may be a radical photoinitiator, in particular a radical photoinitiator having Norrish type I activity and/or Norrish type II activity, more particularly a radical photoinitiator having Norrish type I activity.

Non-limiting types of radical photoinitiators suitable for use in the curable compositions of the present invention include, for example, benzoins, benzoin ethers, acetophenones, α-hydroxy acetophenones, benzyl, benzyl ketals, anthraquinones, phosphine oxides, acylphosphine oxides, α-hydroxyketones, phenylglyoxylates, α-aminoketones, benzophenones, thioxanthones, xanthones, acridine derivatives, phenazene derivatives, quinoxaline derivatives, triazine compounds, benzoyl formates, aromatic oximes, metallocenes, acylsilyl or acylgermanyl compounds, camphorquinones, polymeric derivatives thereof, and mixtures thereof.

Examples of suitable radical photoinitiators include, but are not limited to, 2-methylanthraquinone, 2-ethylanthraquinone, 2-chloroanthraquinone, 2-benzyanthraquinone, 2-t-butylanthraquinone, 1,2-benzo-9,10-anthraquinone, benzyl, benzoins, benzoin ethers, benzoin, benzoin methyl ether, benzoin ethyl ether, benzoin isopropyl ether, alpha-methylbenzoin, alpha-phenylbenzoin, Michler's ketone, acetophenones such as 2,2-dialkoxybenzophenones and 1-hydroxyphenyl ketones, benzophenone, 4,4'-bis-(diethylamino) benzophenone, acetophenone, 2,2-diethyloxyacetophenone, diethyloxyacetophenone, 2-isopropylthioxanthone, thioxanthone, diethyl thioxanthone, 1,5-acetonaphthylene, benzil ketone, α-hydroxy keto, 2,4,6-trimethylbenzoyldiphenyl phosphine oxide, benzyl dimethyl ketal, 2,2-dimethoxy-1,2-diphenylethanone, 1-hydroxycylclohexyl phenyl ketone, 2-methyl-1-[4-(methylthio) phenyl]-2-morpholinopropanone-1, 2-hydroxy-2-methyl-1-phenyl-propanone, oligomeric α-hydroxy ketone, benzoyl phosphine oxides, phenylbis(2,4,6-trimethylbenzoyl)phosphine oxide, ethyl(2,4,6-trimethylbenzoyl)phenyl phosphinate, anisoin, anthraquinone, anthraquinone-2-sulfonic acid, sodium salt monohydrate, (benzene) tricarbonylchromium, benzil, benzoin isobutyl ether, benzophenone/1-hydroxycyclohexyl phenyl ketone, 50/50 blend, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino) benzophenone, camphorquinone, 2-chlorothioxanthen-9-one, dibenzosuberenone, 4,4'-dihydroxybenzophenone, 2,2-dimethoxy-2-phenylacetophenone, 4-(dimethylamino) benzophenone, 4,4'-dimethylbenzil, 2,5-dimethylbenzophenone, 3,4-dimethylbenzophenone, diphenyl(2,4,6-trimethylbenzoyl)phosphine oxide/2-hydroxy-2-methylpropiophenone, 50/50 blend, 4'-ethoxyacetophenone, 2,4,6-trimethylbenzoyldiphenylphophine oxide, phenyl bis(2,4,6-trimethyl benzoyl)phosphine oxide, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, (cumene)cyclopentadienyl iron (ii) hexafluorophosphate, 9,10-diethoxy and 9,10-dibutoxyanthracene, 2-ethyl-9,10-dimethoxyanthracene, thioxanthen-9-one and combinations thereof.

In particular, the photoinitiator other than b) may comprise a radical photoinitiator selected from a benzophenone such as SpeedCure® BP (benzophenone), SpeedCure® 7005 (polymeric benzophenone), SpeedCure® 7006 (polymeric benzophenone), SpeedCure® EMK (4,4'-bis(diethylamino)benzophenone) or SpeedCure® BMS (4-benzoyl-4'-methyldiphenyl sulphide); a thioxanthone such as SpeedCure® 7010 (polymeric thioxanthone), SpeedCure® ITX (isopropyl thioxanthone), SpeedCure® DETX (2,4-diethylthioxanthone) or SpeedCure® CPTX (1-chloro-4-propoxythioxanthone); an α-hydroxy acetophenone; an acylphosphine oxide such as SpeedCure® BPO (phenyl bis(2,4,6-trimethylbenzoyl)-phosphine oxide), SpeedCure® TPO (2,4,6-trimethylbenzoyldiphenylphosphine oxide) or SpeedCure® TPO-L (ethyl (2,4,6-trimethylbenzoyl)phenyl phosphinate); a phenylglyoxylate such as SpeedCure® MBF (methylbenzoylformate); and mixtures thereof.

The photoinitiator other than b) may comprise an acylphosphine oxide, in particular Speedcure TPO-L (ethyl (2,4,6-trimethylbenzoyl)phenyl phosphinate).

The photoinitiator other than b) may comprise a thioxanthone, in particular SpeedCure® ITX (isopropyl thioxanthone) or SpeedCure® DETX (2,4-diethylthioxanthone).

The photoinitiator other than b) may comprise a benzophenone, in particular SpeedCure® EMK (4,4'-bis(diethylamino)benzophenone) or SpeedCure® BMS (4-benzoyl-4'-methyldiphenyl sulphide).

The photoinitiator other than b) may comprise a phenylglyoxylate, in particular SpeedCure® MBF (methylbenzoylformate). The photoinitiator other than b) may comprise a cationic photoinitiator. A cationic photoinitiator is advantageously present when the composition comprises a cationically polymerizable compound as defined above.

The curable composition may comprise a cationic photoinitiator and be substantially free of cationically polymerizable compound. As used herein the term "substantially free of cationically polymerizable compound" means that the curable composition comprises less than 10%, less than 5% less than 2% less than 1%, less than 0.5%, less than 0.1%, less than 0.1% or even 0%, by weight of cationically polymerizable compound based on the weight of the curable composition.

Suitable cationic photoinitiators include any type of photoinitiator that, upon exposure to radiation such as actinic radiation, forms cations (e.g., Bronsted or Lewis acids) that initiate the reaction of the monomeric and (if present) oligomeric cationically polymerizing organic substances in the curable composition. For example, a cationic photoinitiator may be comprised of a cationic portion and an anionic portion. The cationic portion of the photoinitiator molecule can be responsible for the absorption of UV radiation while the anionic portion of the molecule becomes a strong acid after UV absorption.

In particular, the photoinitiator other than b) may be a cationic photoinitiator selected from onium salts with anions of weak nucleophilicity, such as halonium salts or sulfonium salts (e.g., triarylsulfonium salts such as triarylsulfonium hexafluoroantimonate salts); sulfoxonium salts; diazonium salts; metallocene salts; and mixtures thereof.

Halonium salts are of particular interest even when the curable composition is substantially free of cationically polymerizable compound. A halonium salt is an ionic compound comprising a halonium cation (i.e. a halogen atom carrying a positive charge). The halonium cation may be represented by the general structure R—X$^+$—R', where X is a halogen, preferably iodine, and R and R' are any group, preferably an aryl. The halonium cation may be cyclic or an open chain molecular structure. Halonium cations comprising a fluorine, chlorine, bromine, and iodine atom are respectively called fluoronium, chloronium, bromonium, and iodonium. The counter-ion of the salt may be any type of anion such as Cl$^-$, Br$^-$, I$^-$, fluoroalkyl-SO$_3^-$, ArylSO$_3^-$, SbF$_6^-$, SbF$_5$OH$^-$, AsF$_6^-$, PF$_6^-$, BF$_4^-$ or B(C$_6$F$_5$)$_4^-$. Mixtures of iodonium salts can be used if desired. Preferred iodonium salts include diaryliodonium salts such as diphenyliodonium chloride, diphenyliodonium hexafluorophosphate, diphenyliodonium hexafluoroantimonate, diphenyliodonium tetrafluoroborate, di(4-methylphenyl)iodonium tetrafluoroborate; phenyl-4-methylphenyliodonium tetrafluoroborate; di(4-heptylphenyl)iodonium tetrafluoroborate; di(3-nitrophenyl)iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; di(4-methylphenyl) iodonium hexafluorophosphate; diphenyliodonium, hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; 2,2'-diphenyliodonium tetrafluoroborate; di(2,4-dichlorophenyl) iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate. Particularly preferred iodonium salts are diaryliodonium hexafluorophosphate, diaryliodonium hexafluoroantimonate, 4-octyloxyphenyl phenyliodonium hexafluoroantimonate, 4-(2-hydroxytetradecyloxyphenyl) phenyliodonium hexafluoroantimonate, and 4-(1-methylethyl)phenyl 4-methylphenyliodonium tetrakis(pentafluorophenyl)borate.

The photoinitiator other than b) may comprise a iodonium salt, in particular a diaryliodonium salt, more particularly bis(4-tert-butylphenyl)iodonium hexafluorophosphate.

The photoinitiator other than b) may comprise a mixture of a thioxanthone and a iodonium salt, in particular a mixture of isopropylthioxanthone and bis (4-tert-butylphenyl)iodonium hexafluorophosphate The amount of photoinitiator other than b) may be varied as may be appropriate depending on the photoinitiator(s) selected, the amounts and types of polymerizable species present in the curable composition, the radiation source and the radiation conditions used, among other factors. Typically, however, the amount of photoinitiator other than b) may be from 0% to 5%, in particular 0.1% to 3%, more particularly 0.5 to 2%, by weight based on the total weight of the curable composition. For example, the amount of photoinitiator other than b) may be from 0.01% to 5%, from 0.02% to 3%, from 0.05 to 2%, from 0.1 to 1.5% or from 0.2 to 1%, by weight based on the total weight of the curable composition. In another example, the amount of photoinitiator other than b) may be from 1% to 5%, from 1.5% to 5%, from 2 to 5%, from 2.5 to 5% or from 3 to 5%, by weight based on the total weight of the curable composition When the composition comprises a mixture of photoinitiators other than b) the amount of each photoinitiator other than b) may be from 0.01% to 5%, from 0.02% to 3%, from 0.05 to 2%, from 0.1 to 1.5% or from 0.2 to 1%, by weight based on the total weight of the curable composition. The total amount of photoinitiator other than b) may be from 0.01 to 10%, from 0.1 to 9%, from 0.2 to 8%, from 0.5 to 7% or from 1 to 6%, by weight based on the total weight of the curable composition.

Additives

The curable composition of the present invention may comprise an additive. The curable composition may comprise a mixture of additives.

In particular, the additive may be selected from sensitizers, amine synergists, antioxidants/photostabilizers, light blockers/absorbers, polymerization inhibitors, foam inhibitors, flow or leveling agents, colorants, pigments, dispersants (wetting agents, surfactants), slip additives, fillers, chain transfer agents, thixotropic agents, matting agents, impact modifiers, waxes, mixtures thereof, and any other additives conventionally used in the coating, sealant, adhesive, molding, 3D printing or ink arts.

The curable composition may comprise a sensitizer.

Sensitizers may be introduced in the curable composition of the present invention in order to extend the sensitivity of the photoinitiator to longer wavelengths. For example, the sensitizer may absorb light at longer or shorter wavelengths than the photoinitiator and be capable of transferring the energy to the photoinitiator and revert to its ground state. Photoinitiators other than b) are not encompassed by the term sensitizer.

Examples of suitable sensitizers include anthracenes and carbazoles.

The concentration of sensitizer in the curable composition will vary depending on the photoinitiator that is used. Typically, however, the curable composition is formulated to comprise from 0% to 5%, in particular 0.1% to 3%, more particularly 0.5 to 2%, by weight of sensitizer based on the total weight of the curable composition.

The curable composition may comprise an amine synergist.

Amine synergists may be introduced in the curable composition of the present invention in order to act synergistically with Norrish Type II photoinitiators and/or to reduce oxygen inhibition. Amine synergists are typically tertiary amines. When used in conjunction with Norrish Type II photoinitiators, the tertiary amine provides an active hydrogen donor site for the excited triple state of the photoinitiator, thus producing a reactive alkyl-amino radical which can subsequently initiate polymerization. Tertiary amines are also able to convert unreactive peroxy species, formed by reaction between oxygen and free radicals, to reactive alkyl-amino radicals, thus reducing the effects of oxygen on curing. When the composition comprises a cationically polymerizable compound, amine synergists may not be present.

Examples of suitable amine synergists include low-molecular weight tertiary amines (i.e. having a molecular weight of less than 200 g/mol) such as triethanol amine, N-methyldiethanol amine. Other types of amine synergists are aminobenzoates or amine-modified acrylates (acrylated amines formed by Michael addition of secondary amines on part of the acrylate groups carried by acrylate functionalized monomers and/or oligomers). Examples of aminobenzoates include ethyl-4-(N,N'-dimethylamino) benzoate (EDB), 2-n-butoxyethyl 4-(dimethylamino) benzoate (BEDB). Examples of commercially available amine-modified acrylate oligomers include CN3705, CN3715, CN3755, CN381 and CN386, all available from Arkema. Polymeric or multi-amino versions are also suitable.

The concentration of amine synergist in the curable composition will vary depending on the type of compound that is used. Typically, however, the curable composition is formulated to comprise from 0% to 25%, from 0.1% to 10%, from 0.5% to 8%, from 0.5% to 5%, more particularly still 1 to 5%, by weight of amine synergist based on the total weight of the curable composition.

In one embodiment, the curable composition from 1 to 10%, from 1.5 to 8%, from 2 to 7%, from 2.5 to 6% or from 3 to 5%, by weight of amine synergist based on the weight of the curable composition.

In an alternative embodiment, the curable composition may be substantially free of amine synergist. For example, the curable composition comprises less than 1%, less than 0.5% less than 0.25% less than 0.2%, less than 0.1%, less than 0.05%, less than 0.01% or even 0%, by weight of amine synergist based on the weight of the curable composition.

The curable composition may comprise a chain-transfer agent.

Chain-transfer agents may be introduced in the curable composition of the present invention in order to increase the curing speed. In particular, the chain-transfer agent may be a polythiol compound. Any compound having at least two thiol (—SH) functional groups may be advantageously used as a polythiol compound in the curable compositions of the present invention. For example, the polythiol compound may contain three or more thiol groups, four or more thiol groups or five or more thiol groups. In certain embodiments, no more than ten thiol groups, no more than eight thiol groups or no more than six thiol groups are present in the polythiol compound. Thus, in various embodiments, the polythiol compound contains two to ten or three to eight thiol groups. The polythiol compound may, in certain embodiments, contain three, four, five or six thiol groups.

The polythiol may have a molecular weight of at least 350 g/mol, at least 375 g/mol, at least 400 g/mol, at least 425 g/mol or at least 450 g/mol and/or has a molecular weight not greater than 2000 g/mol, not greater than 1750 g/mol, not greater than 1500 g/mol, not greater than 1250 g/mol or not greater than 1000 g/mol. For example, the polythiol may have a molecular weight of from 350 g/mol to 2000 g/mol or from 400 g/mol to 1000 g/mol.

Suitable polythiols for use in the present invention may also be characterized with respect to their thiol equivalent weight (calculated by dividing the molecular weight of the polythiol by the number of thiol functional groups per molecule). In various embodiments of the invention, the polythiol compound has a thiol equivalent weight of at least 80 g/mol, at least 90 g/mol, at least 95 g/mol or at least 100 g/mol and/or a thiol equivalent weight of not more than 450 g/mol, not more than 400 g/mol, not more than 350 g/mol, not more than 300 g/mol, not more than 250 g/mol or not more than 200 Dal g/mol tons. For example, the thiol equivalent weight of the polythiol compound may be from 80 g/mol to 450 g/mol, from 90 g/mol to 400 g/mol or from 100 g/mol to 200 g/mol.

Additionally, it will generally be desirable to select a polythiol compound or combination of polythiol compounds having low odor. For example, the polythiol(s) may be sufficiently low in odor that the coating or sealant composition containing the polythiol(s) does not have any sulfur odor discernable to a human olfactory system when the composition is spread as a layer on a substrate surface at 25° C. In other embodiments, the polythiol compound(s) used has a relatively high flash point, e.g., a flash point of at least 100° C. as measured by ASTM D92-12b.

According to various embodiments of the invention, the polythiol compound may be a monomer, an oligomer or a polymer (i.e., the backbone or skeleton of the polythiol compound may be monomeric, oligomeric or polymeric in character). Each thiol group may be attached to the skeleton or backbone of the polythiol compound either directly or via a linking moiety.

In certain embodiments of the present invention, the polythiol compound is a thiol-functionalized ester of a polyalcohol (a compound containing two or more alcohol functional groups).

The following may be mentioned by way of example as polyalcohols suitable for esterifying with a thiol-functionalized carboxylic acid to provide a polythiol compound: alkanediols, such as butanediol, pentanediol, hexanediol, alkylene glycols, such as ethylene glycol, propylene glycol and polypropylene glycol, glycerin, 2-(hydroxyl methyl)propane-1,3-diol, 1,1,1,-tris(hydroxymethyl)ethane, 1,1,1-trimethylolpropane, di(trimethylolpropane), tricyclodecane dimethylol, 2,2,4-trimethyl-1,3-pentanediol, bisphenol A, cyclohexane dimethanol, alkoxylated and/or ethoxylated and/or propoxylated derivatives of neopentyl glycol, tetraethylene glycol cyclohexanedimethanol, hexanediol, 2-(hydroxymethyl)propane-1,3-diol, 1,1,1-tris(hydroxymethyl)ethane, 1,1,1-trimethylolpropane and castor oil, pentaerythritol, sugars, sugar alcohols or mixtures thereof.

In particular, suitable polythiol compounds include esters of α-thioacetic acid (2-mercaptoacetic acid), β-thiopropionic acid (3-mercaptopropionic acid) and 3-thiobutyric acid (3-mercaptobutyric acid), wherein such acids are esterified with diols, triols, tetraols, pentaols or other polyols, such as 2-hydroxy-3-mercaptopropyl derivatives of diols, triols, tetraols, pentaols or other polyols. Mixtures of alcohols may also be used as a basis for the thiol-functionalized compound. In this respect, reference is made to the WO 99/51663 A1 publication, the contents of which are incorporated by reference in this application.

Particularly examples of suitable polythiol compounds which may be mentioned are: glycol-bis(2-mercaptoacetate), glycol-bis(3-mercaptopropionate), 1,2-propylene glycol-bis(2-mercaptoacetate), 1,2-propylene glycol-bis(3-mercaptopropionate), 1,3-propylene glycol-bis(2-mercaptoacetate), 1,3-propylene glycol-bis(3-mercaptopropionate), tris(hydroxymethyl) methane-tris(2-mercaptoacetate), tris(hydroxymethyl)methane-tris(3-mercaptopropionate), 1,1,1-tris(hydroxymethyl) ethane-tris(2-mercaptoacetate), 1,1,1-tris(hydroxymethyl)ethane-tris(3-mercaptopropionate), 1,1,1-trimethylolpropane-tris(2-mercaptoacetate), ethoxylated 1,1,1-trimethylolpropane-tris(2-mercaptoacetate), propoxylated 1,1,1-trimethylolpropane-tris(2-mercaptoacetate), 1,1,1-trimethylolpropane-tris(3-mercaptopropionate), ethoxylated 1,1,1-trimethylolpropane-tris(3-mercaptopropionate), propoxylated trimethylolpropane-tris(3-mercaptopropionate), 1,1,1-trimethylolpropane-tris(3-mercaptobutyrate), pentaerythritol-tris(2-mercaptoacetate), pentaerythritol-tetrakis(2-mercaptoacetate), pentaerythritol-tris(3-mercaptopropionate), pentaerythritol-tetrakis(3-mercaptopropionate), pentaerythritol-tris(3-mercaptobutyrate), pentaerythritol-tetrakis(3-mercaptobutyrate), Capcure® 3-800 (BASF), GPM-800 (Gabriel Performance Products), Capcure® LOF (BASF), GPM-800LO (Gabriel Performance Products), KarenzMT PE-1 (Showa Denko), 2-ethylhexylthioglycolate, iso-octylthioglycolate, di(n-butyl) thiodiglycolate, glycol-di-3-mercaptopropionate, 1,6-hexanedithiol, ethylene glycol-bis(2-mercaptoacetate) and tetra (ethylene glycol)dithiol.

Such polythiol compounds may be prepared by any method known in the art or obtained from commercial sources, such as the polythiols sold under the trade name "Thiocure®" by Bruno Bock.

The polythiol compound may be used alone or as a combination of two or more different polythiol compounds.

The amount of polythiol in the curable composition will vary depending on the type of compound that is used. Typically, however, the curable composition is formulated to comprise from 0.1 to 10%, from 0.5 to 8%, from 1 to 5% or from 1.5 to 4%, by weight of polythiol based on the weight of the curable composition.

The curable composition may comprise a stabilizer.

Stabilizers may be introduced in the curable composition of the present invention in order to provide adequate storage stability and shelf life. Advantageously, one or more such stabilizers are present at each stage of the method used to prepare the curable composition, to protect against unwanted reactions during processing of the ethylenically unsaturated components of the curable composition. As used herein, the term "stabilizer" means a compound or substance which retards or prevents reaction or curing of actinically-curable functional groups present in a composition in the absence of actinic radiation. However, it will be advantageous to select an amount and type of stabilizer such that the composition remains capable of being cured when exposed to actinic radiation (that is, the stabilizer does not prevent radiation curing of the composition). Typically, effective stabilizers for purposes of the present invention will be classified as free radical stabilizers (i.e., stabilizers which function by inhibiting free radical reactions).

Any of the stabilizers known in the art related to (meth) acrylate-functionalized compounds may be utilized in the present invention. Quinones represent a particularly preferred type of stabilizer which can be employed in the context of the present invention. As used herein, the term "quinone" includes both quinones and hydroquinones as well as ethers thereof such as monoalkyl, monoaryl, monoaralkyl and bis(hydroxyalkyl) ethers of hydroquinones. Hydroquinone monomethyl ether is an example of a suitable stabilizer which can be utilized. Other stabilizers known in the art such as BHT and derivatives, phosphite compounds, phenothiazine (PTZ), triphenyl antimony and tin(II) salts can also be used.

The concentration of stabilizer in the curable composition will vary depending upon the particular stabilizer or combination of stabilizers selected for use and also on the degree of stabilization desired and the susceptibility of components in the curable compositions towards degradation in the absence of stabilizer. Typically, however, the curable composition is formulated to comprise from 5 to 5000 ppm stabilizer. According to certain embodiments of the invention, the reaction mixture during each stage of the method employed to make the curable composition contains at least some stabilizer, e.g., at least 10 ppm stabilizer.

The curable composition may comprise a light blocker (sometimes referred to as a light absorber).

The introduction of a light blocker is particularly advantageous when the curable composition is to be used as a resin in a three-dimensional printing process involving photocuring of the curable composition. The light blocker may be any such substances known in the three-dimensional printing art, including for example non-reactive pigments and dyes. The light blocker may be a visible light blocker or a UV light blocker, for example. Examples of suitable light blockers include, but are not limited to, titanium dioxide, carbon black and organic ultraviolet light absorbers such as hydroxybenzophenone, hydroxyphenylbenzotriazole, oxanilide, hydroxyphenyltriazine, Sudan I, bromothymol blue, 2,2'-(2,5-thiophenediyl)bis(5-tert-butylbenzoxazole) (sold under the brand name "Benetex OB Plus") and benzotriazole ultraviolet light absorbers.

The amount of light blocker may be varied as may be desired or appropriate for particular applications. Generally speaking, if the curable composition contains a light blocker, it is present in a concentration of from 0.001 to 10% by weight based on the weight of the curable composition.

Advantageously, the curable compositions of the present invention may be formulated to be solvent-free, i.e., free of any non-reactive volatile substances (substances having a boiling point at atmospheric pressure of 150° C. or less). For example, the curable compositions of the present invention may contain little or no non-reactive solvent, e.g., less than 10% or less than 5% or less than 1% or even 0% non-reactive solvent, based on the total weight of the curable composition. As used herein, the term non-reactive solvent means a solvent that does not react when exposed to the actinic radiation used to cure the curable compositions described herein.

According to other advantageous embodiments of the invention, the curable composition is formulated to be useable as a one component or one part system. That is, the curable composition is cured directly and is not combined with another component or second part (such as an amine monomer, as defined in U.S. Pat. Application Publication No. 2017/0260418 A1) prior to being cured.

Curable Composition

In a first embodiment, the curable composition of the invention may comprise:
 a) an ethylenically unsaturated compound;
 b) a phosphine oxide photoinitiator having both Norrish Type I and Norrish type II activity;
 c) optionally a radical photoinitiator other than b);
 d) optionally a halonium salt;
 e) optionally an additive.

In particular, the curable composition of the first embodiment comprises at least one component selected from c), d), e) and mixtures thereof. For example, the curable composition of the first embodiment may comprise at least one component selected from a radical photoinitiator other than b), a halonium salt, an additive and mixtures thereof.

More particularly, the curable composition comprises at least one component selected from a radical photoinitiator other than b), a halonium salt, an amine synergist, a chain-transfer agent, a mixture of radical photoinitiators other than b), a mixture of a radical photoinitiator other than b) and a halonium salt and a mixture of an amine synergist and a radical photoinitiator other than b).

Preferably, the ethylenically unsaturated compound a) of the first embodiment consists essentially of a mixture of one or more (meth)acrylate-functionalized monomers and one or more (meth)acrylate-functionalized oligomers. More preferably, the ethylenically unsaturated compound a) comprises at least one mono(meth)acrylate-functionalized monomer, at least one (meth)acrylate-functionalized monomer containing two or more, preferably 3 or more, (meth)acrylate groups per molecule and at least one (meth)acrylate-functionalized urethane oligomer.

Preferably, the photoinitiator b) of the first embodiment has the following structure:

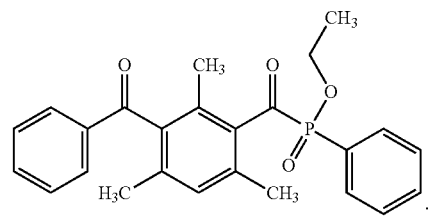 [SMILES: CCOP(=O)(C(=O)c1c(C)cc(C)c(C(=O)c2ccccc2)c1C)c1ccccc1]

Preferably, the radical photoinitiator other than b) of the first embodiment comprises a radical photoinitiator selected from a thioxanthone, a benzophenone, a phenylglyoxylate and mixtures thereof.

Preferably, the halonium salt of the first embodiment comprises an iodonium salt.

Preferably, the amine synergist of the first embodiment comprises an aminobenzoate or an amine-modified acrylate.

Preferably, the chain-transfer agent of the first embodiment comprises a polythiol.

The curable composition of the first embodiment may comprise or consist essentially of:
 a1) 10-80%, in particular 15-75%, more particularly 20-70%, of one or more (meth)acrylate-functionalized monomers;
 a2) 10-80%, in particular 15-75%, more particularly 20-70%, of one or more (meth)acrylate-functionalized oligomers;
 b) 0.05-10%, in particular 0.1-5%, more particularly 0.5-2%, of a phosphine oxide photoinitiator having both Norrish Type I and Norrish type II activity;

c) 0-5%, in particular 0.1-3%, more particularly 0.5-2%, of a radical photoinitiator other than b);
d) 0-5%, in particular 0.1-3%, more particularly 0.5-2%, of a halonium salt;
e) 0-30% of one or more additives;

wherein the % are % by weight based on the weight of the composition.

When the curable composition comprises a radical photoinitiator other than b), the curable composition of the first embodiment may comprise or consist essentially of:
- a1) 10-80%, in particular 15-75%, more particularly 20-70%, of one or more (meth)acrylate-functionalized monomers;
- a2) 10-80%, in particular 15-75%, more particularly 20-70%, of one or more (meth)acrylate-functionalized oligomers;
- b) 0.05-10%, in particular 0.1-5%, more particularly 0.5-2%, of a phosphine oxide photoinitiator having both Norrish Type I and Norrish type II activity;
- c) 0.01-5%, in particular 0.02-3%, more particularly 0.05-2%, of a radical photoinitiator other than b);
- d) 0-5% of a halonium salt;
- e) 0-30% of one or more additives, wherein the % are % by weight based on the weight of the composition.

When the curable composition comprises a mixture of a radical photoinitiator other than b) and a halonium salt, the curable composition of the first embodiment may comprise or consist essentially of:
- a1) 10-80%, in particular 15-75%, more particularly 20-70%, of one or more (meth)acrylate-functionalized monomers;
- a2) 10-80%, in particular 15-75%, more particularly 20-70%, of one or more (meth)acrylate-functionalized oligomers;
- b) 0.05-10%, in particular 0.1-5%, more particularly 0.5-2%, of a phosphine oxide photoinitiator having both Norrish Type I and Norrish type II activity;
- c) 0.01-5%, in particular 0.02-3%, more particularly 0.05-2%, of a radical photoinitiator other than b);
- d) 0.01-5%, in particular 0.02-3%, more particularly 0.05-2%, of a halonium salt;
- e) 0-30% of one or more additives, wherein the % are % by weight based on the weight of the composition.

When the curable composition comprises an amine synergist, the curable composition of the first embodiment may comprise or consist essentially of:
- a1) 10-80%, in particular 15-75%, more particularly 20-70%, of one or more (meth)acrylate-functionalized monomers;
- a2) 10-80%, in particular 15-75%, more particularly 20-70%, of one or more (meth)acrylate-functionalized oligomers;
- b) 0.05-10%, in particular 0.1-5%, more particularly 0.5-2%, of a phosphine oxide photoinitiator having both Norrish Type I and Norrish type II activity;
- c) 0-5% of a radical photoinitiator other than b);
- d) 0-5%, of a halonium salt;
- e1) 0.1-10%, in particular 0.5-8%, more particularly 1-5% of amine synergist;
- e2) 0 to 30 of additives other than e1);

wherein the % are % by weight based on the weight of the composition.

When the curable composition comprises a polythiol, the curable composition of the first embodiment may comprise or consist essentially of:
- a1) 10-80%, in particular 15-75%, more particularly 20-70%, of one or more (meth)acrylate-functionalized monomers;
- a2) 10-80%, in particular 15-75%, more particularly 20-70%, of one or more (meth)acrylate-functionalized oligomers;
- b) 0.05-10%, in particular 0.1-5%, more particularly 0.5-2%, of a phosphine oxide photoinitiator having both Norrish Type I and Norrish type II activity;
- c) 0-5% of a radical photoinitiator other than b);
- d) 0-5%, of a halonium salt;
- e1) 0.1-10%, in particular 0.5-8%, more particularly 1-5% of polythiol;
- e2) 0 to 30 of additives other than e1);

wherein the % are % by weight based on the weight of the composition.

When the curable composition comprises a mixture of a photoinitiator other than b) and an amine synergist, the curable composition of the first embodiment may comprise or consist essentially of:
- a1) 10-80%, in particular 15-75%, more particularly 20-70%, of one or more (meth)acrylate-functionalized monomers;
- a2) 10-80%, in particular 15-75%, more particularly 20-70%, of one or more (meth)acrylate-functionalized oligomers;
- b) 0.05-10%, in particular 0.1-5%, more particularly 0.5-2%, of a phosphine oxide photoinitiator having both Norrish Type I and Norrish type II activity;
- c) 0.01-5%, in particular 0.02-3%, more particularly 0.05-2%, of a radical photoinitiator other than b);
- d) 0-5%, of a halonium salt;
- e1) 0.1-10%, in particular 0.5-8%, more particularly 1-5% of amine synergist;
- e2) 0 to 30 of additives other than e1);

wherein the % are % by weight based on the weight of the composition.

Preferably, the composition of the first embodiment does not comprise any component other than components a1), a2), b), c), d), e), e1) and e2), when present. Accordingly, the total weight of components a1), a2), b), c), d), e), e1) and e2), when present, may represent 100% of the weight of the composition.

Such a composition may be cured by means of free radical polymerization.

In second embodiment, the curable composition of the invention may comprise
- a') an ethylenically unsaturated compound;
- b') a phosphine oxide photoinitiator having both Norrish Type I and Norrish type II activity;
- c') a cationically polymerizable compound;
- d1') a cationic photoinitiator;
- d2') optionally a radical photoinitiator other than b); and
- e') optionally an additive.

Preferably, the ethylenically unsaturated compound a) of the second embodiment consists essentially of one or more (meth)acrylate-functionalized monomers and optionally one or more (meth)acrylate-functionalized oligomers.

The curable composition of the second embodiment may comprise or consist essentially of:
- a1') 10-80%, in particular 15-75%, more particularly 20-70%, of one or more (meth)acrylate-functionalized monomers;
- a2') 0-50%, in particular 5-40%, more particularly 10-30%, of one or more (meth)acrylate-functionalized oligomers;

b') 0.05-10%, in particular 0.1-5%, more particularly 0.5-2%, of a phosphine oxide photoinitiator having both Norrish Type I and Norrish type II activity;

c') 10-80%, in particular 15-75%, more particularly 20-70%, of one or more cationically polymerizable compounds;

d1') 0.05-5%, in particular 0.1-3%, more particularly 0.5-2%, of a cationic photoinitiator;

d'2) 0-5%, in particular 0.1-3%, more particularly 0.5-2%, of a radical photoinitiator other than b);

e') 0-30% of one or more additives;

wherein the % are % by weight based on the weight of the composition.

Preferably, the composition of the second embodiment does not comprise any component other than components a1')-e'). Accordingly, the total weight of components a1'), a2'), b'), c'), d') and e') may represent 100% of the weight of the composition.

The composition of the second embodiment may be cured by free radical polymerization and cationic polymerization.

In preferred embodiments of the invention, the curable composition is a liquid at 25° C. In various embodiments of the invention, the curable compositions described herein are formulated to have a viscosity of less than 10,000 mPa·s (cP), or less than 5,000 mPa·s (cP), or less than 4,000 mPa·s (cP), or less than 3,000 mPa·s (cP), or less than 2,500 mPa·s (cP), or less than 2,000 mPa·s (cP), or less than 1,500 mPa·s (cP), or less than 1,000 mPa·s (cP) or even less than 500 mPa·s (cP) as measured at 25° C. using a Brookfield viscometer, model DV-II, using a 27 spindle (with the spindle speed varying typically between 20 and 200 rpm, depending on viscosity). In advantageous embodiments of the invention, the viscosity of the curable composition is from 200 to 5,000 mPa·s (cP), or from 200 to 2,000 mPa·s (cP), or from 200 to 1,500 mPa·s (cP), or from 200 to 1,000 mPa·s (cP) at 25° C. Relatively high viscosities can provide satisfactory performance in applications where the curable composition is heated above 25° C., such as in three-dimensional printing operations or the like which employ machines having heated resin vats.

The curable compositions described herein may be compositions that are to be subjected to curing by means of free radical polymerization, cationic polymerization or other types of polymerization. In particular embodiments, the curable compositions are photocured (i.e., cured by exposure to actinic radiation such as light, in particular visible or UV light).

The curable composition of the invention may be an ink, coating, sealant, adhesive, molding, or 3D printing composition, in particular a 3D-printing composition or a nail coating composition.

End use applications for the curable compositions include, but are not limited to, inks, coatings, adhesives, additive manufacturing resins (such as 3D printing resins), molding resins, sealants, composites, antistatic layers, electronic applications, recyclable materials, smart materials capable of detecting and responding to stimuli, packaging materials, personal care articles, nail coatings, articles for use in agriculture, water or food processing, or animal husbandry, and biomedical materials. The curable compositions of the invention thus find utility in the production of biocompatible articles. Such articles may, for example, exhibit high biocompatibility, low cytotoxicity and/or low extractables.

The composition according to the invention may in particular be used to obtain a cured product, a 3D printed article or a nail coating according to the following processes.

Process for the Preparation of a Cured Product, a 3D-Printed Article and a Nail Coating The process for the preparation of a cured product according to the invention comprises curing the composition of the invention. In particular, the composition may be cured by exposing the composition to radiation. More particularly, the composition may be cured by exposing the composition to UV, near-UV, visible, infrared and/or near-infrared radiation or to an electron beam.

Curing may be accelerated or facilitated by supplying energy to the curable composition, such as by heating the curable composition. Thus, the cured product may be deemed the reaction product of the curable composition, formed by curing. A curable composition may be partially cured by exposure to actinic radiation, with further curing being achieved by heating the partially cured article. For example, an article formed from the curable composition (e.g., a 3D printed article) may be heated at a temperature of from 40° C. to 120° C. for a period of time of from 5 minutes to 12 hours.

Prior to curing, the curable composition may be applied to a substrate surface in any known conventional manner, for example, by spraying, knife coating, roller coating, casting, drum coating, dipping, and the like and combinations thereof. Indirect application using a transfer process may also be used. A substrate may be any commercially relevant substrate, such as a high surface energy substrate or a low surface energy substrate, such as a metal substrate or plastic substrate, respectively. The substrates may comprise metal, paper, cardboard, glass, thermoplastics such as polyolefins, polycarbonate, acrylonitrile butadiene styrene (ABS), and blends thereof, composites, wood, leather and combinations thereof. When used as an adhesive, the curable composition may be placed between two substrates and then cured, the cured composition thereby bonding the substrates together to provide an adhered article. Curable compositions in accordance with the present invention may also be formed or cured in a bulk manner (e.g., the curable composition may be cast into a suitable mold and then cured).

The cured product obtained with the process of the invention may be an ink, a coating, a sealant, an adhesive, a molded article or a 3D-printed article.

In particular, the cured product may be a 3D-printed article. A 3D-printed article may be defined as an article obtained with a 3D-printer using a computer-aided design (CAD) model or a digital 3D model.

The 3D-printed article may, in particular, be obtained with a process for the preparation of a 3D-printed article that comprises printing a 3D article with the composition of the invention. In particular, the process may comprise printing a 3D article layer by layer or continuously.

A plurality of layers of a curable composition in accordance with the present invention may be applied to a substrate surface; the plurality of layers may be simultaneously cured (by exposure to a single dose of radiation, for example) or each layer may be successively cured before application of an additional layer of the curable composition.

The curable compositions which are described herein can be used as resins in three-dimensional printing applications. Three-dimensional (3D) printing (also referred to as additive manufacturing) is a process in which a 3D digital model is manufactured by the accretion of construction material. The 3D printed object is created by utilizing the computer-aided design (CAD) data of an object through sequential construction of two dimensional (2D) layers or slices that correspond to cross-sections of 3D objects. Stereolithography (SL) is one type of additive manufacturing where a liquid resin is hardened by selective exposure to a radiation to form each 2D layer. The radiation can be in the form of electromagnetic waves or an electron beam. The most commonly applied energy source is ultraviolet, visible or infrared radiation.

Sterolithography and other photocurable 3D printing methods typically apply low intensity light sources to radiate each layer of a photocurable resin to form the desired article. As a result, photocurable resin polymerization kinetics and the green strength of the printed article are important criteria if a particular photocurable resin will sufficiently polymerize (cure) when irradiated and have sufficient green strength to retain its integrity through the 3D printing process and post-processing.

The curable compositions of the invention are especially useful as 3D printing resin formulations, that is, compositions intended for use in manufacturing three-dimensional articles using 3D printing techniques. Such three-dimensional articles may be free-standing/self-supporting and may consist essentially of or consist of a composition in accordance with the present invention that has been cured. The three-dimensional article may also be a composite, comprising at least one component consisting essentially of or consisting of a cured composition as previously mentioned as well as at least one additional component comprised of one or more materials other than such a cured composition (for example, a metal component or a thermoplastic component or inorganic filler or fibrous reinforcement). The curable compositions of the present invention are particularly useful in digital light printing (DLP), although other types of three-dimensional (3D) printing methods may also be practiced using the inventive curable compositions (e.g., SLA, inkjet, multi-jet printing, piezoelectric printing, actinically-cured extrusion, and gel deposition printing). The curable compositions of the present invention may be used in a three-dimensional printing operation together with another material which functions as a scaffold or support for the article formed from the curable composition of the present invention.

Thus, the curable compositions of the present invention are useful in the practice of various types of three-dimensional fabrication or printing techniques, including methods in which construction of a three-dimensional object is performed in a step-wise or layer-by-layer manner. In such methods, layer formation may be performed by solidification (curing) of the curable composition under the action of exposure to radiation, such as visible, UV or other actinic irradiation. For example, new layers may be formed at the top surface of the growing object or at the bottom surface of the growing object. The curable compositions of the present invention may also be advantageously employed in methods for the production of three-dimensional objects by additive manufacturing wherein the method is carried out continuously. For example, the object may be produced from a liquid interface. Suitable methods of this type are sometimes referred to in the art as "continuous liquid interface (or interphase) product (or printing)" ("CLIP") methods. Such methods are described, for example, in WO 2014/126830; WO 2014/126834; WO 2014/126837; and Tumbleston et al., "Continuous Liquid Interface Production of 3D Objects," Science Vol. 347, Issue 6228, pp. 1349-1352 (Mar. 20, 2015), the entire disclosure of which is incorporated herein by reference in its entirety for all purposes.

When stereolithography is conducted above an oxygen-permeable build window, the production of an article using a curable composition in accordance with the present invention may be enabled in a CLIP procedure by creating an oxygen-containing "dead zone" which is a thin uncured layer of the curable composition between the window and the surface of the cured article as it is being produced. In such a process, a curable composition is used in which curing (polymerization) is inhibited by the presence of molecular oxygen; such inhibition is typically observed, for example, in curable compositions which are capable of being cured by free radical mechanisms. The dead zone thickness which is desired may be maintained by selecting various control parameters such as photon flux and the optical and curing properties of the curable composition. The CLIP process proceeds by projecting a continuous sequence of actinic radiation (e.g., UV) images (which may be generated by a digitial light-processing imaging unit, for example) through an oxygen-permeable, actinic radiation- (e.g., UV-) transparent window below a bath of the curable composition maintained in liquid form. A liquid interface below the advancing (growing) article is maintained by the dead zone created above the window. The curing article is continuously drawn out of the curable composition bath above the dead zone, which may be replenished by feeding into the bath additional quantities of the curable composition to compensate for the amounts of curable composition being cured and incorporated into the growing article.

In another embodiment, the curable composition will be supplied by ejecting it from a printhead rather than supplying it from a vat. This type of process is commonly referred to as inkjet or multijet 3D printing. One or more UV curing sources mounted just behind the inkjet printhead cures the curable composition immediately after it is applied to the build surface substrate or to previously applied layers. Two or more printheads can be used in the process which allows application of different compositions to different areas of each layer. For example, compositions of different colors or different physical properties can be simultaneously applied to create 3D printed parts of varying composition. In a common usage, support materials—which are later removed during post-processing—are deposited at the same time as the compositions used to create the desired 3D printed part. The printheads can operate at temperatures from about 25° C. up to about 100° C. Viscosities of the curable compositions are less than 30 mPa·s at the operating temperature of the printhead.

The process for the preparation of a 3D-printed article may comprise the steps of:
a) providing (e.g., coating) a first layer of a curable composition in accordance with the present invention onto a surface;
b) curing the first layer, at least partially, to provide a cured first layer;
c) providing (e.g., coating) a second layer of the curable composition onto the cured first layer;
d) curing the second layer, at least partially, to provide a cured second layer adhered to the cured first layer; and
e) repeating steps c) and d) a desired number of times to build up the three-dimensional article.

Although the curing steps may be carried out by any suitable means, which will in some cases be dependent upon the components present in the curable composition, in certain embodiments of the invention the curing is accomplished by exposing the layer to be cured to an effective amount of radiation, in particular actinic radiation (e.g., electron beam radiation, UV radiation, visible light, etc.). The three-dimensional article which is formed may be heated in order to effect thermal curing.

Accordingly, in various embodiments, the present invention provides a process comprising the steps of:

a) providing (e.g., coating) a first layer of a curable composition in accordance with the present invention and in liquid form onto a surface;
b) exposing the first layer imagewise to actinic radiation to form a first exposed imaged cross-section, wherein the radiation is of sufficient intensity and duration to cause at least partial curing of the layer in the exposed areas;
c) providing (e.g., coating) an additional layer of the curable composition onto the previously exposed imaged cross-section;
d) exposing the additional layer imagewise to actinic radiation to form an additional imaged cross-section, wherein the radiation is of sufficient intensity and duration to cause at least partial curing of the additional layer in the exposed areas and to cause adhesion of the additional layer to the previously exposed imaged cross-section;
e) repeating steps c) and d) a desired number of times to build up the three-dimensional article.

After the 3D article has been printed, it may be subjected to one or more post-processing steps. The post-processing steps can be selected from one or more of the following steps removal of any printed support structures, washing with water and/or organic solvents to remove residual resins, and post-curing using thermal treatment and/or actinic radiation either simultaneously or sequentially. The post-processing steps may be used to transform the freshly printed article into a finished, functional article ready to be used in its intended application.

In an alternative embodiment, the cured product may be a nail coating.

The nail coating may, in particular, be obtained with a process for coating nails comprising applying the curable composition according the invention on a nail, and curing the composition on the nail.

The cured product, 3D-printed articles and nail coatings obtained with the processes of the invention are described herein after.

Cured Product, 3D-Printed Article and Nail Coating

The cured product of the invention is obtained by curing the composition of the invention or according to the process of the invention.

The cured product may be an ink, a coating, a sealant, an adhesive, a molded article or a 3D-printed article. In particular, the cured product may be a 3D-printed article or a nail coating.

Uses

The composition of the invention may be used to obtain an ink, a coating, a sealant, an adhesive, a molded article or a 3D-printed article, in particular a 3D-printed article or a nail coating.

The invention also relates to the use of a phosphine oxide photoinitiator having both Norrish Type I and Norrish type II activity in a 3D printing composition or 3D printing process.

The invention also relates to the use of a phosphine oxide photoinitiator having both Norrish Type I and Norrish type II activity in a nail polish composition or a nail coating process.

The phosphine oxide photoinitiator having both Norrish Type I and Norrish type II activity may correspond to phosphine oxide photoinitiator b) as defined above. In particular, it may be according to formula (I) as defined above.

The phosphine oxide photoinitiator may advantageously be associated with one or more ethylenically unsaturated compounds, in particular one or more ethylenically unsaturated compounds selected from one or more (meth)acrylate-functionalized monomers, one or more (meth)acrylate-functionalized oligomers and mixtures thereof, and optionally one or more cationically polymerizable compounds. The ethylenically unsaturated compounds and the optional cationically polymerizable compounds may be as defined above. The 3D printing composition or nail polish composition may further comprise a photoinitiator other than b). The photoinitiator other than b) may be as defined above. The 3D printing composition or nail polish composition may further comprise an additive. The additive may be as defined above.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

The invention is illustrated with the following non-limiting examples.

EXAMPLES

Materials

Raw materials used in the examples are as described below:

| Materials name | Chemical name | Supplier/Manufacturer |
|---|---|---|
| SR494 | Ethoxylated Pentaerythritol Tetraacrylate | Sartomer |
| CN991 | Aliphatic urethane acrylate oligomer | Sartomer |
| SR531 | Cyclic trimethylol formal acrylate | Sartomer |
| CN374 | Amine modified acrylate | Sartomer |
| CN1968 | Difunctional urethane methacrylate | Sartomer |
| SR399 | Dipenterythritol pentaacrylate | Sartomer |
| SR349 | 3EO Bis-phenol A Diacrylate | Sartomer |
| CN386 | Acrylated Amine Coinitiator | Sartomer |

| Materials name | Chemical name | Supplier/Manufacturer |
| --- | --- | --- |
| HEMA | 2-Hydroxyethyl Methacrylate | Sartomer |
| CN3715LM | Acrylated Amine Coinitiator | Sartomer |
| SpeedCure ® TPO | Diphenyl(2,4,6-trimethylbenzoyl)phosphine oxide | Sartomer-Lambson |
| SpeedCure ® BPO | Phenyl bis(2,4,6-trimethylbenzoyl)-phosphine oxide | Sartomer-Lambson |
| SpeedCure ® TPO-L | Ethyl (2,4,6-trimethylbenzoyl) phenyl phosphinate | Sartomer-Lambson |
| SpeedCure ® XKm | Ethyl(3-benzoyl-2,4,6-trimethylbenzoyl) (phenyl) phosphinate | Sartomer-Lambson |
| SpeedCure ® 2-ITX | 2-Isopropylthioxanthone | Sartomer-Lambson |
| SpeedCure ® DETX | 2,4-Diethylthioxanthone | Sartomer-Lambson |
| SpeedCure ® EMK | 4,4'-bis(diethylamino)benzophenone | Sartomer-Lambson |
| SpeedCure ® MBF | Methylbenzoylformate | Sartomer-Lambson |
| SpeedCure ® BMS | 4-Benzoyl-4'-methyldiphenyl sulphide | Sartomer-Lambson |
| SpeedCure ® 938 | Bis(4-tert-butylphenyl)iodonium hexafluorophosphate | Sartomer-Lambson |
| SpeedCure ® 7040 | Polymeric Aminobenzoate Mixture | Sartomer-Lambson |
| Thiocure ® PETMP | Pentaerythritol Tetra-(3-Mercaptopropionate) | Bruno Bock Thiochemicals |
| Tinuvin ® CarboProtect ® | 2-(2-hydroxyphenyl)-benzotriazole derivative | BASF |
| Milliken Red Dye | Reactint ® Red X64 | Milliken Chemical |

Methods and Sample Preparation

Working Curves

Working curves were measured using the method below to find the Ec (Critical Energy) and Dp (Depth of Penetration) which are key characteristics used to determine printability and printer settings for successful 3D printing. Ec represents the amount of energy that needs to be applied to cure a formulation to a "green state" and Dp is the depth the UV photons penetrate the formulation which determines the thickness of the layer that can be printed.

Working curves and 3D printing were done on an EnvisionOne 3D printer from EnvisionTec with a 385 nm light source.

Preparing the Printing Files
1. Import an STL file that has measurable squares of varying thicknesses (in the same increment as the layer thickness being printed).
2. For the below STL file, use 50 µm layer thickness in the slicing software. This will ensure that each printed square receives a linear increase in energy dosage.
3. Import the STL file to the printer slicing software.
4. Place the part in a known build area, for example in the center.
5. Place the part on the surface, and do not use any support structures, rafts, or base plates.
6. Set the burn in exposure and standard exposure to be equal to each other.
7. Minimize other settings like elevator wait times to make the procedure quick and efficient.

Preparing the Printer
1. Remove the build platform.
2. Install the vat.
3. Place resin in the vat-only a small amount to cover ~0.6 cm of the bottom of the vat is needed.

Print Working-Curve Parts
1. Start the working-curve print file.
2. Once the print is complete, carefully peel off the part from the bottom of the vat surface.
3. Gently clean the part with IPA (isopropyl alcohol), TPM (tripropylene glycol monomethyl ether), acetone, or other solvent.
4. Print 2-3 working-curves for each formulation.

Measuring the Cure Depths for Corresponding Energy Dosages
1. A dial indicator with a comparator stand was used to measure the cure depths of all squares. Generally speaking, with an increase in energy dosage there should be an increase in cure depth thickness.
2. The energy dosages were determined as follows:
   a. Energy dosage (mJ/cm$^2$)=irradiance (mW/cm$^2$)*time (seconds)
   b. Note: energy dosage can also be measured with a radiometer

| Projector Intensity (mW/cm$^2$): 5.6 | | |
| --- | --- | --- |
| Time of exposure(s) | Exposure (mJ/cm$^2$) | Thickness (mils) |
| 1 | 5.6 | 2.76 |
| 2 | 11.2 | 4.61 |
| 3 | 16.7 | 5.55 |
| 4 | 22.3 | 6.26 |
| 5 | 27.9 | 6.77 |
| 6 | 33.5 | 7.13 |
| 7 | 39.1 | 7.60 |
| 8 | 44.6 | 7.91 |
| 9 | 50.2 | 8.11 |

Determining Critical Exposure, Penetration Depth, and Print Parameters
1. The Jacobs working-curve equation, described in P. F. Jacobs, Fundamentals of stereolithography, Proc. Solid Free. Fabr. Symp. (1992) 87-89, was used to determine critical exposure, Ec (mJ/cm$^2$), and penetration depth, Dp (mils).
   a.

$$C_d = D_p \ln\left(\frac{E_{max}}{E_c}\right)$$

b. Where,
      i. $C_d$=measured cure depths (mils)
      ii. $E_{max}$=energy dosages (mJ/cm$^2$)
   c. Plot $C_d$ (mils) vs. $\ln(E_{max})$. The slope of the plot corresponds to the penetration depth and the $E_{max}$ point that corresponds to $C_d$=0 is the critical exposure.

2. The measured cure depths and corresponding exposure times were used to determine the optimal print parameters. Target an exposure time that achieves a cure depth 2-4× the layer thickness to print with.
3. Example: for the above energy dosage and cure depth measurements, the Dp=2.4 mils and the Ec=0.6 mJ/cm².

Tensile Sample Preparation and Testing
1. 400 g of each formulation was prepared as showed in Table 6 according to standard method
2. The burn-in range and standard range exposure times of EnvisionOne cDLP Mechanical (385 nm) from Envision Tec were verified.
3. The printer was set up with the following parameters
   Printer irradiance: ~5.5 mW/cm²
   Elevator settings: default
   Part printing orientation: XZ plane
   4 seconds/layer
4. Dog bone shape of tensile bars were printed
   Specimen type: ASTM D638 Type IV
   Number of specimens printed: 5×2
   Size: approximately 115 mm×19 mm×3.2 mm (L×W×T).
5. A set of 5 specimen was kept as green tensile bar for both tensile test and FTIR test.
6. Another set of 5 tensile bars was put in Dymax Model 5000 Flood Cure Unit for UVA/UVV flood cure, each side cured for 60 seconds.
7. The tensile bars were stored in a control room with 23° C. and 50% RH for 40~80 hours before testing.

Tensile tester (ASTM D618): Instron 5966 w/ 2630-109 static axial clip-on extensometer.
   Speed of testing: 5 mm/min
   Pre-load: 5N
   Pre-load pull rate: 0.1 mm/min
   Specimen protect: Yes
   Specimen protect load: 4.448 N
   Extensometer: Yes
   Extensometer type: Instron 2630-109 (ASTM E83 Class B-1 extensometer)
   Extensometer gauge length: 1"

All five bars were tested, the average tensile data was calculated.

FTIR Testing

A Fourier Transform Infrared (FTIR) with an Attenuated Total Reflection (ATR) setup was used. All polymerization rate measurements were performed using Nicolet iS50 FT-IR Spectrometer from Thermo Scientific, equipped with a standard DLaTGS detector. For measurement, a drop of liquid sample was placed in the center of an ATR crystal to collect IR spectrum, then a flat surface of a printed green part was pressed over ATR crystal to collect a new IR spectrum for acrylate conversion calculation. Measurements were taken at the area under the reference peak around 1720 cm$^{-1}$; the acrylate peak at approximately 1407 cm$^{-1}$ was also measured. Peak area was determined using the baseline technique where a baseline is chosen to be tangent to absorbance minima on either side of the peak. The area under the peak and above the baseline was then determined. The integration limits for liquid and the cured sample are not identical but are similar, especially for the reference peak.

The ratio of the acrylate peak area to the reference peak were determined for both the liquid and the cured samples. Degree of cure or conversion, expressed as percentage reacted acrylate unsaturation, was calculated from the equation below:

$$\text{Conversion (\%)} = [(R_{liq} - R_{grn}) \times 100]/R_{liq}$$

Where $R_{liq}$ is the area ratio of the liquid sample and $R_{grn}$ is the area ratio of the cured green tensile bar. The resulting acrylate conversions were tested using the FTIR method described as above.

Example 1: Comparison of SpeedCure® XKm to Other Phosphine Oxide Initiators

A model monomer/oligomer blend shown in Table 1 was used to evaluate and compare Ec/Dp performance of XKm, TPO, TPO-L and BAPO photoinitiators.

TABLE 1

|  | Component | Wt % |
|---|---|---|
| Blend 1 | SR494 | 55 |
|  | CN991 | 30 |
|  | SR531 | 15 |

UV curable formulations were prepared by adding varying amounts of photoinitiator to Blend 1 (amount of photoinitiator is indicated in % by weight based on the weight of Blend 1). The formaulations were mixed on a Flacteck mixer and warmed as needed to fully dissolve all solids. Formulations and Ec/Dp results are shown in Table 2.

TABLE 2

|  | Initiator (wt %) | Ec (mJ/cm²) | Dp (mils) |
|---|---|---|---|
| Blend 1 + XKm | 0.5 | 47.42 | 75.30 |
|  | 2 | 14.18 | 19.52 |
|  | 6 | 5.69 | 6.50 |
| Blend 1 + TPO | 0.5 | 4.27 | 24.57 |
|  | 2 | 4.12 | 5.99 |
|  | 6 | 1.45 | 1.77 |
| Blend 1 + TPO-L | 0.5 | 28.42 | 51.90 |
|  | 2 | 8.18 | 13.20 |
|  | 6 | 3.17 | 4.29 |
| Blend 1 + BAPO | 0.5 | 6.63 | 20.53 |
|  | 2 | 1.54 | 3.98 |
|  | 6 | 0.72 | 1.32 |

Example 2: Acceleration of Cure by Addition of Amine Synergist

Figure 2:
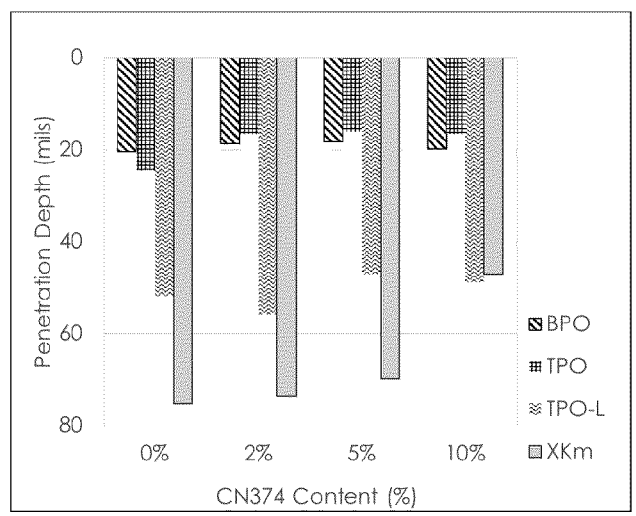
FIG. 2 shows the penetration depth (Dp) for the formulations of Example 2.

To determine the effectiveness of the Norrish Type II activity of XKm, an amine synergist (CN374) was added to the 0.5% initiator blends of Table 2 (amount of amine synergist is indicated in % by weight based on the weight of the initiator blend containing 0.5 parts by weight of photoinitiator and 100 parts by weight of Blend 1) and the Ec/Dp values were measured. The results shown in Table 3 and FIGS. 1 and 2 show that XKm has a stronger response to CN374 amine synergist than TPO, TPO-L or BAPO indicating that its Type II functionality is important in the curing process along with Type I behavior exhibited by all four of the initiators. At 2% loading of CN374 in the XKm blend, the reactivity as measured by Ec was similar to higher than that obtained with the other three initiators without any added amine synergist. At the same time, the Dp with XKm was much greater under all conditions which allows creation of thicker layers during 3D printing. Therefore, the use of XKm with a small amount of amine synergist leads to shorter printing time for a 3D printed part as fewer layers need to be printed while the time to cure each layer will be the same.

TABLE 3

| | CN374 (wt %) | Ec (mJ/cm²) | Dp (mils) |
|---|---|---|---|
| Blend 1 + 0.5% XKm | 0 | 47.42 | 75.30 |
| | 2 | 4.14 | 73.78 |
| | 5 | 2.81 | 69.93 |
| | 10 | 1.93 | 47.19 |
| Blend 1 + 0.5% TPO | 0 | 4.27 | 24.57 |
| | 2 | 0.82 | 16.59 |
| | 5 | 0.67 | 16.25 |
| | 10 | 0.78 | 16.64 |

TABLE 3-continued

| | CN374 (wt %) | Ec (mJ/cm²) | Dp (mils) |
|---|---|---|---|
| Blend 1 + 0.5% TPO-L | 0 | 28.42 | 51.90 |
| | 2 | 2.86 | 55.85 |
| | 5 | 1.76 | 47.15 |
| | 10 | 1.94 | 48.89 |
| Blend 1 + 0.5% BAPO | 0 | 6.63 | 20.53 |
| | 2 | 1.06 | 18.74 |
| | 5 | 0.83 | 18.39 |
| | 10 | 0.87 | 19.87 |

Example 3: 3D Printing Using SpeedCure® XKm

Figure 3:
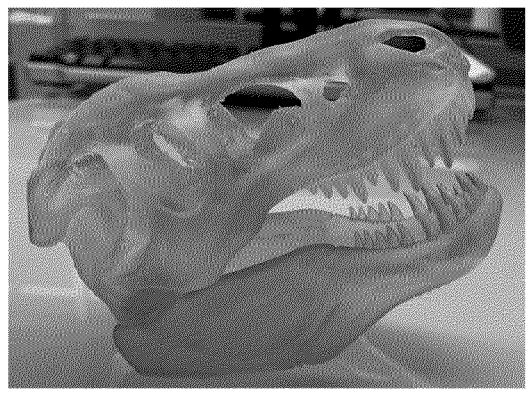
FIG. 3 shows the 3D article printed in Example 3.

The formulation shown in Table 4 was used to successfully 3D print the part shown in FIG. 3. The printing was done on an EnvisionOne printer with print parameters of: Irradiance=5.4 mW/cm², Layer Thickness=50 μm and Exposure=1 sec/layer. The printed part had good green strength after printing and was non-tacky with good surface finish after cleaning and post-curing.

TABLE 4

| Component | Wt % |
|---|---|
| SR494 | 52.6 |
| CN991 | 31.6 |
| SR531 | 15.8 |
| CN374 | +5 |
| XKm | +4 |
| CarboProtect | +0.011 |
| Milliken Red Dye | +0.001 |

Example 4: Curing Performance without Use of an Amine Synergist

Figure 4:
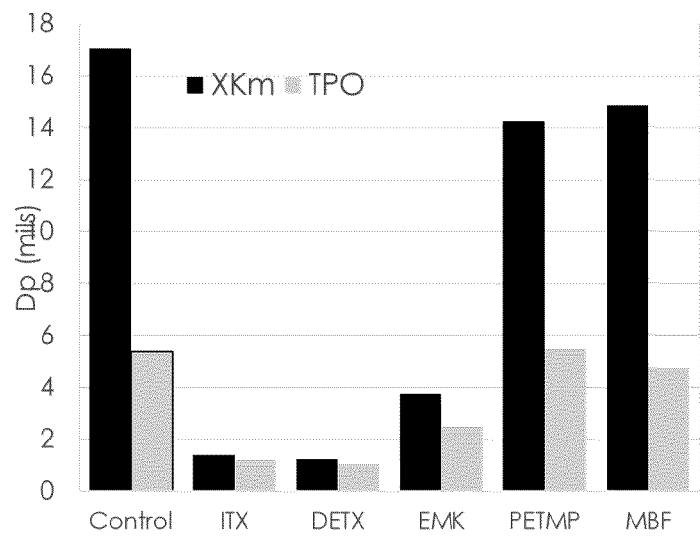
FIG. 4 shows the penetration depth (Dp) for the formulations of Example 4.
Figure 5:
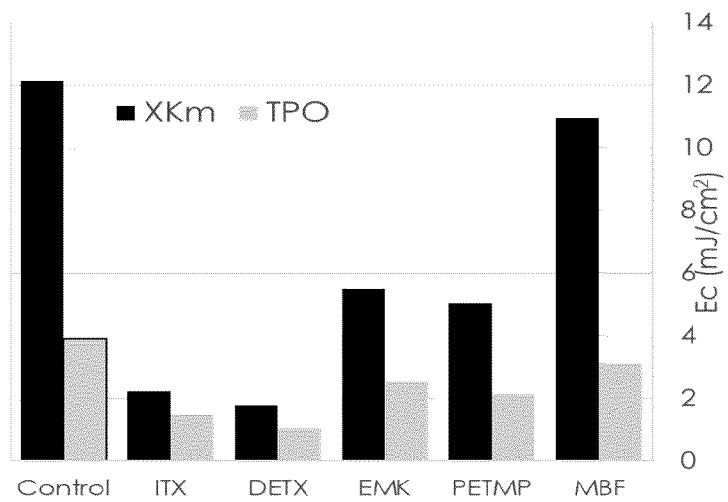
FIG. 5 shows the critical exposure (Ec) for the formulations of Example 4.
Figure 6:
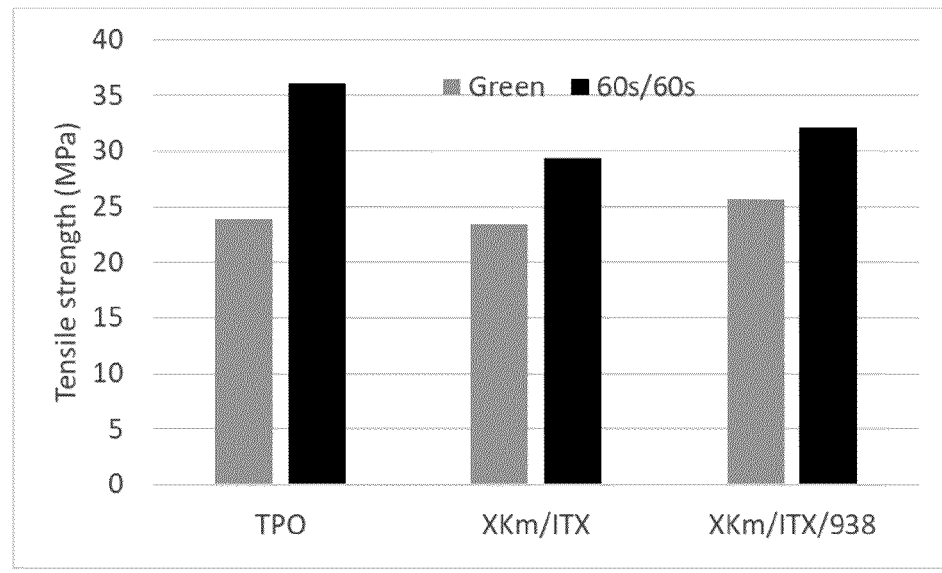
FIG. 6 shows the green and postcured tensile strength for the formulations of Example 5.
Figure 7:
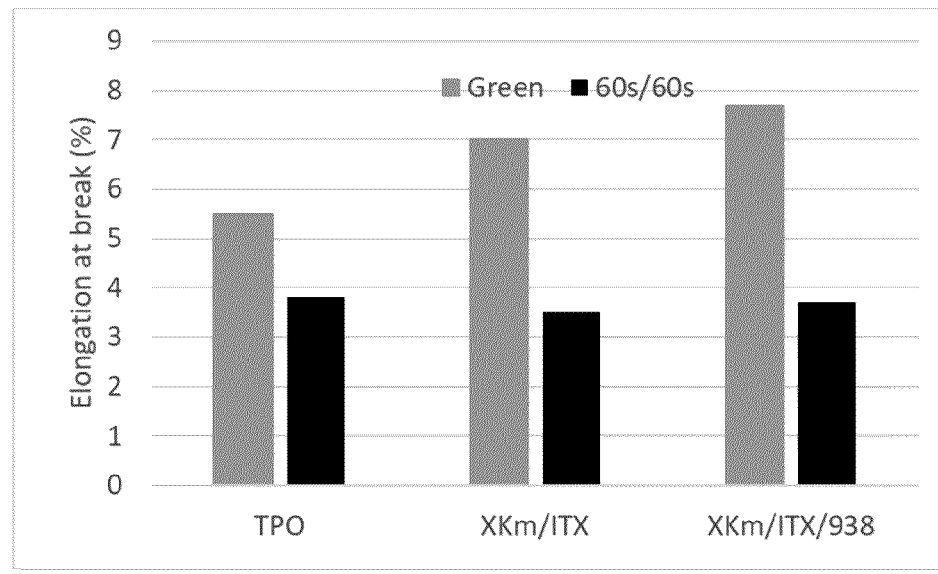
FIG. 7 shows the green and postcured tensile elongation for the formulations of Example 5.
Figure 8:
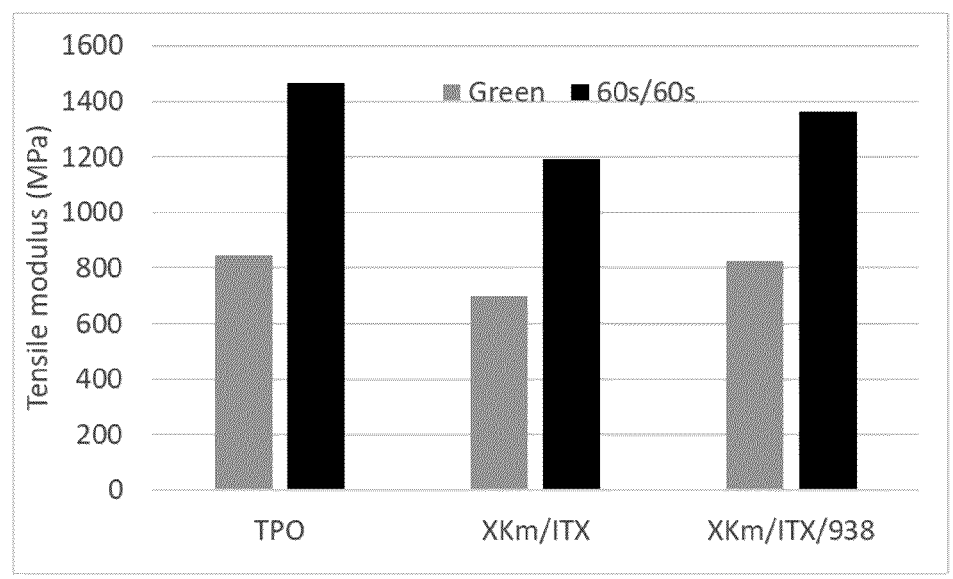
FIG. 8 shows the green and postcured tensile modulus for the formulations of Example 5.

In some cases it is not possible or desirable to use an amine synergist in a formulation. In these cases, other photoinitiators or chain transfer agents can be used to enhance cure initiation with XKm. Two master batch blends TPO-MB and XKM-MB were prepared by adding 2 parts by weight of TPO or XKm to 100 parts by weight of Blend 1. The other photoinitiators or chain-transfer agents were added to the master blends as shown in Table 5 (amounts are in parts by weight) and the Ec/Dp were measured as described above. The results in Table 5 and FIGS. 4 and 5 show that addition of a thioxanthone photoinitiator (SpeedCure® ITX or SpeedCure® DETX) has a much larger effect on Ec/Dp of XKm vs TPO and makes the curing behavior of the two nearly equivalent. These results show that the combination of XKm with a thioxanthone photoinitiator is a viable alternative to TPO for 3D printing. Ec/Dp values with a benzophenone photoinitiator (SpeedCure® EMK) or a chain-transfer agent (Thiocure PETMP) are also strongly affected and indicate that they can also be used to enhance cure initiation of XKm.

TABLE 5

| | | | | | | | | | | | | |
|---|---|---|---|---|---|---|---|---|---|---|---|---|
| TPO-MB (Control) | 100 | | 100 | | 100 | | 100 | | 100 | | 100 | |
| XKm-MB (Control) | | 100 | | 100 | | 100 | | 100 | | 100 | | 100 |
| SpeedCure ® ITX | | | 0.5 | 0.5 | | | | | | | | |
| SpeedCure ® DETX | | | | | 0.5 | 0.5 | | | | | | |
| SpeedCure ® EMK | | | | | | | 0.1 | 0.1 | | | | |
| Thiocure PETMP | | | | | | | | | 2 | 2 | | |
| SpeedCure ® MBF | | | | | | | | | | | 2 | 2 |
| Dp (mils) | 5.36 | 17.05 | 1.23 | 1.40 | 1.06 | 1.24 | 2.52 | 3.74 | 5.53 | 14.22 | 4.77 | 14.84 |
| Ec (mJ/cm²) | 3.89 | 12.11 | 1.50 | 2.23 | 1.07 | 1.75 | 2.56 | 5.50 | 2.13 | 5.02 | 3.12 | 10.95 |

Example 5: 3D Printed Green and Postcured Physical Properties with XKm/ITX or XKm/ITX/Iodonium 3D printing compositions and their performances are shown in Examples 5.1, 5.2 and Comparative Example 1 (CEx 5). These examples illustrate the effects of addition to XKm containing formulations of thioxanthone and of a mixture of thioxanthone and iodonium salt (SpeedCure® 938) on the green and post cured physical properties of 3D printed parts.

TABLE 6

| Materials | CEx 5 (wt %) | Ex 5.1 (wt %) | Ex 5.2 (wt %) |
|---|---|---|---|
| Blend 1 | 100 | 100 | 100 |
| SpeedCure ® TPO | 4 | | |
| SpeedCure ® XKm* | | 4.83 | 4.83 |
| SpeedCure ® ITX | | 0.2 | 0.2 |
| SpeedCure ® 938 | | | 1.0 |
| Dp (mils) | 2.56 | 2.51 | 2.30 |
| Ec (mJ/cm²) | 1.65 | 2.69 | 2.95 |
| Conversion (Printed green part, %) | 47.39 | 39.16 | 56.59 |
| Tensile strength (Printed green part, MPa) | 23.8 | 23.4 | 25.6 |
| Elongation at break (Printed green part, %) | 5.5 | 7.0 | 7.7 |
| Tensile modulus (Printed green part, MPa) | 844.9 | 698.2 | 823.3 |
| Tensile strength (60 s/60 s postcured, MPa) | 36.1 | 29.3 | 32.1 |
| Elongation at break (60 s/60 s postcured, %) | 3.8 | 3.5 | 3.7 |
| Tensile modulus (60 s/60 s postcured, MPa) | 1463.9 | 1192.2 | 1363.1 |

*Equal molar concentration vs. SpeedCure ® TPO

1. Ex 5.1 vs CEx 5: At equal molar concentration of phosphine oxide in the formulation, 0.2% ITX, as other photoinitiator, was added into XKm to obtain the similar Dp, slightly higher Ec. Tests showed that it gave lower acrylate conversion from 47.39% of CEx 5 to 39.16% of Ex 5.1. Both green parts and postcured parts gave lower tensile properties when using XKm.
2. Ex 5.2 vs Ex 1: Addition of an iodonium salt in Ex 5.2 gave both slightly lower Dp and higher Ec, but in a reasonably similar range. Tests showed that iodonium salt boosted up acrylate conversion of XKm/ITX from 39.16% for Ex 5.1 to 56.59% for Ex 5.2, with is higher than CEx 5. Both green parts and postcured parts gave better tensile properties, very close to CEx 5 (within a statistical difference range). It concluded a three-component photoinitiator package containing XKm, thioxanthone and iodonium salt can print the same parts with similar mechanical properties as TPO photoinitiator.

Example 6: SpeedCure® Xkm for UV-Curable Nail Coatings—Reactivity

SpeedCure® XKm was compared to SpeedCure® TPO-L in a UV curable nail gel top coat. A typical UV curable nail gel top coat formulation is shown below. CN1968 is a urethane methacrylate oligomer that has a good balance of adhesion, optical clarity and tensile properties. The urethane methacrylate oligomer was mixed with pentafunctional monomer $SR^{399}$ (DiPEPA), $SR^{349}$ (EO3BPADA) and 2-hydroxyethyl methacrylate (HEMA). A formulation containing a 3% by weight loading of TPO-L with respect to the weight of the (meth)acrylate monomers and oligomers was compared to formulations containing 1%, 3% or 5% by weight loadings of SpeedCure® XKm.

TABLE 7

Nail gel topcoat formulations

| | CEx 6 (wt %) | Ex 6.1 (wt %) | Ex 6.2 (wt %) | Ex 6.3 (wt %) |
|---|---|---|---|---|
| CN1968 | 45 | 45 | 45 | 45 |
| SR399 | 20 | 20 | 20 | 20 |
| SR349 | 10 | 10 | 10 | 10 |
| HEMA | 22 | 24 | 22 | 20 |
| TPO-L | 3 | | | |
| XKm | | 1 | 3 | 5 |

The formulations were drawn down using a 3MIL draw down bar on glass panels and cured in a LED nail lamp (Gelish 18G, λ—395-405 nm) for 60 seconds each. The color, haze and yellowness of the compositions were measured using HunterLab Ultrascan VIS spectrophotometer. Hardness was measured using a Konig pendulum on surface of coating before and after IPA wipe. LED curable compositions may have a tacky layer on the surface due to oxygen inhibition. The tacky layer was removed with IPA to determine the hardness of the coating. The performance properties of the UV curable nail gel top coat are shown below.

Compositions containing higher loadings of SpeedCure® XKm had a slight yellow color to the film, which was measured by the yellowness value (b*) and APHA color values in the colorimeter. The hardness values for Example 6.2 and Comparative example 6 were similar before and after IPA wipe.

Photo Differential Scanning calorimetry (PhotoDSC) was used to measure the cure speed, heat generation during cure and heat flow measurements for the UV curable top coat compositions containing TPO-L and SpeedCure® XKm. PhotoDSC was measured using a TA instruments Q2000 DSC equipped with an EFOS A4000 Acticure UV/Visible light curing system containing a 100 W Mercury lamp light source. The UV-light intensity was measured out of the sample window using an EIT UV power puck II radiometer prior to the experiment. Sample preparation for PhotoDSC occurred as follows: A Tzero aluminum reference pan and a Tzero aluminum sample pan were weighed. One drop of formulation (about 10-20 milligrams) was placed at the center of the sample pan and the mass was recorded. The two pans were placed in the DSC apparatus. The system was stabilized at 25° C. for 30 seconds under a continuous stream of nitrogen. An isothermal experiment was initiated and sample and reference pan were pulsed with 1 second of UV/Visible light (320-450 nm, 190-210 mw/cm$^2$). An exothermic peak, due to crosslinking, is recorded with each pulse. Subsequent pulses occur until the exothermic peak height was similar for consecutive pulses. The cure speed is measured by counting the number of pulses it takes for the samples to achieve similar heat flow values (J/g). The max temperature during cure is recorded from the first pulse. Surface tack was measured qualitatively by coating the comparative and inventive compositions on a plastic nail spoon and curing them using the LED nail lamp for 60 s. Tack was assessed on a 0-5 scale, with 0=no tack and 5=very tacky.

TABLE 8

Nail gel topcoat performance properties

| | CEx 6 (3% TPO-L) | Ex 6.1 (1% XKm) | Ex 6.2 (3% XKm) | Ex 6.3 (5% XKm) |
|---|---|---|---|---|
| Film Clarity | clear | clear | sl. yellow | sl. yellow |
| Color (APHA, film) | 6.77 | 8.18 | 14.33 | 20.26 |
| Haze (%, film) | 0.22 | 0.12 | 0.17 | 0.28 |
| Yellowness (b*, film) | 0.45 | 0.54 | 1.00 | 1.44 |
| Hardness (Konig, avg.) before IPA wipe | 22 | 14 | 19 | 17 |
| Hardness (Konig, avg.) after IPA wipe | 61 | 44 | 54 | 57 |

TABLE 9

Nail gel topcoat formulation reactivity as measured by photo-DSC

|  | Tack (5 s cure) | Tack (10 s cure) | Tack (60 s cure) | PhotoDSC (Cure speed, # pulses) | PhotoDSC (Max temperature, °C.) | PhotoDSC Exothermic Heat Flow (1st pulse, J/g) |
|---|---|---|---|---|---|---|
| CEx 6 (3% TPO-L) | 3 | 3 | 3 | 3 | 43 | 171.1 |
| Ex 6.1 (1% XKm) | 3 | 3 | 2 | 2 | 49 | 213.8 |
| Ex 6.2 (3% XKm) | 3 | 3 | 3 | 2 | 42 | 167.3 |
| Ex 6.3 (5% XKm) | 2 | 2 | 2 | 3 | 40 | 142.2 |

Examples 6.2 and Comparative example 6 are a direct comparison of a composition containing 3% TPO-L to a composition containing 3% SpeedCure® Xkm. Both compositions had the same surface tack after curing. The cure speed of Example 6.2 was faster and the maximum temperature during cure for the first pulse was lower compared to Comparative example 6.

Example 7: SpeedCure® Xkm for UV Curable Fingernail Coatings—Surface Cure

To increase surface cure of the compositions, new formulations containing SpeedCure® XKm along with another type II photoinitiator, such as SpeedCure® MBF or with an amine synergist, like SpeedCure® 7040, CN386 or CN3715LM were tested. For ease in design of experiments, Prep formulation using CN1968, DiPEPA, EO3BPADA and HEMA was prepared using the same ratios as seen in Table 7. To the Prep formulation was added SpeedCure® XKm along with different combinations of Type II PIs and amine synergists to improve surface cure as shown in Table 10 (amount are in parts by weight).

TABLE 10

|  | Ex 7.4 | Ex 7.5 | Ex 7.6 | Ex 7.7 | Ex 7.8 | Ex 7.9 | Ex 7.10 | Ex 7.11 |
|---|---|---|---|---|---|---|---|---|
| Prep formulation | 25 | 25 | 25 | 25 | 25 | 25 | 25 | 25 |
| SpeedCure ® XKm | 0.75 | 0.75 | 0.75 | 0.75 | 1.25 | 1.25 | 1.25 | 1.25 |
| SpeedCure ® MBF | 0.75 |  |  |  | 1.25 |  |  |  |
| SpeedCure ® 7040 |  | 0.75 |  |  |  | 1.25 |  |  |
| CN386 |  |  | 0.75 |  |  |  | 1.25 |  |
| CN3715LM |  |  |  | 0.75 |  |  |  | 1.25 |

The samples were mixed using the Flacktek high speed mixer at 1500 RPM for two minutes and drawn down using a 3 MIL drawn down bar, similar to Example 6. Performance properties are shown in Table 11. The color and yellowness gave similar values to Example 6. The addition of the amine synergist can cause slight increases to color and yellowness of the coatings. The hardness before IPA wipe was consistent with Example 6. However, the hardness after IPA was lower for all samples compared to Example 6.

TABLE 11

|  | Ex 7.4 | Ex 7.5 | Ex 7.6 | Ex 7.7 | Ex 7.8 | Ex 7.9 | Ex 7.10 | Ex 7.11 |
|---|---|---|---|---|---|---|---|---|
| Film Clarity | clear | clear | clear | clear | clear | clear | clear | clear |
| Color (APHA, film) | 12.61 | 14.39 | 14.73 | 15.88 | 18.01 | 22.47 | 20.92 | 18.70 |
| Haze (%, film) | 0.25 | 0.37 | 0.56 | 0.53 | 0.69 | 0.65 | 0.14 | 1.19 |
| Yellowness (b*, film) | 0.84 | 0.96 | 1.00 | 1.10 | 1.26 | 1.57 | 1.49 | 1.29 |
| Hardness before IPA wipe (Konig, avg.) | 10 | 17 | 18 | 19 | 14 | 15 | 14 | 16 |
| Hardness after IPA wipe (Konig, avg.) | 24 | 29 | 28 | 29 | 24 | 27 | 21 | 22 |

The PhotoDSC showed that all samples were able to cure within two pulses and the max temperature during cure was much lower compared to Example 6. Surface tack was measured on nail spoons after curing for 60 s in the LED nail lamp. Examples 7.4-7.9 still had a measurable amount of surface tack while Examples 7.10 and 7.11 only had very slight surface tack as shown in Table 12.

TABLE 12

| | Tack (60 s cure) | PhotoDSC (Cure speed, # pulses) | PhotoDSC (Max temperature, °C.) | PhotoDSC Exothermic Heat Flow (1st pulse, J/g) |
|---|---|---|---|---|
| Ex 7.4 | 3 | 2 | 35.5 | 165.5 |
| Ex 7.5 | 3 | 2 | 38.6 | 191.5 |
| Ex 7.6 | 3 | 2 | 39.4 | 198.5 |
| Ex 7.7 | 2 | 2 | 39.3 | 212.5 |
| Ex 7.8 | 2 | 3 | 33.6 | 124.4 |
| Ex 7.9 | 2 | 2 | 35.2 | 148.1 |
| Ex 7.10 | 1 | 2 | 36.7 | 172.0 |
| Ex 7.11 | 1 | 2 | 36.3 | 181.2 |

Example 8: Comparison of SpeedCure® Xkm with TPO-L for UV Curable Fingernail Coatings Formulations containing SpeedCure® TPO-L were prepared and compared to formulations containing SpeedCure® XKm with the same Type II PIs and amine synergists as in Example 7. For the purpose of these examples, SpeedCure® DETX was included to help promote additional surface cure compared to Example 7. In addition, these formulations will allow to directly compare the performance properties of SpeedCure® TPO-L to SpeedCure® XKm.

TABLE 13

| | CEx 8.2 | CEx 8.3 | CEx 8.4 | CEx 8.5 | Ex 8.12 | Ex 8.13 | Ex 8.14 | Ex 8.15 |
|---|---|---|---|---|---|---|---|---|
| Prep formulation | 25 | 25 | 25 | 25 | 25 | 25 | 25 | 25 |
| SpeedCure ® TPO-L | 1.25 | 1.25 | 1.25 | 1.25 | | | | |
| SpeedCure ® XKm | | | | | 1.25 | 1.25 | 1.25 | 1.25 |
| SpeedCure ® DETX | 0.1375 | 0.1375 | 0.1375 | 0.1375 | 0.1375 | 0.1375 | 0.1375 | 0.1375 |
| SpeedCure ® MBF | 1.25 | | | | 1.25 | | | |
| SpeedCure ® 7040 | | 1.25 | | | | 1.25 | | |
| CN386 | | | 1.25 | | | | 1.25 | |
| CN3715LM | | | | 1.25 | | | | 1.25 |

The performance properties of Comparative examples 8.2-8.5 and Examples 8.12-8.15 were tested and are shown in Table 14. Hardness results were similar to the previous Example 7. Hardness after an IPA wipe was not measured because the formulations were able to achieve a nearly-to-completely tack free surface. Not needing to remove an undercured tacky layer with a solvent wipe is a significant advantage.

TABLE 14

| | CEx 8.2 | CEx 8.3 | CEx 8.4 | CEx 8.5 | Ex 8.12 | Ex 8.13 | Ex 8.14 | Ex 8.15 |
|---|---|---|---|---|---|---|---|---|
| Film Clarity | clear | clear | clear | clear | clear | clear | clear | clear |
| Color (APHA, film) 20 | 28.02 | 30.58 | 13.76 | 28.00 | 36.84 | 40.80 | 36.68 | 32.49 |
| Haze (%, film) | 0.13 | 0.39 | 0.12 | 3.26 | 3.16 | 0.20 | 0.36 | 0.13 |
| Yellowness (b*, film) | 2.18 | 2.32 | 1.07 | 2.14 | 2.78 | 3.12 | 2.75 | 2.46 |
| Hardness before IPA wipe (Konig, avg.) | 22 | 25 | 29 | 29 | 20 | 23 | 26 | 21 |

The PhotoDSC measurements of Table 15 show that compositions according to the invention containing SpeedCure® XKm had similar cure speed and max temperature during cure as the comparative compositions containing SpeedCure® TPO-L. Surface tack was measured after 60 seconds cure in an LED nail lamp. Examples 8.14 and 8.15 had a tack free surface, similar to Comparative examples 8.4 and 8.5.

TABLE 15

| | Tack (60 s cure) | PhotoDSC (Cure speed, # pulses) | PhotoDSC (Max temperature, °C.) | PhotoDSC Exothermic Heat Flow (1st pulse, J/g) |
|---|---|---|---|---|
| CEx 8.2 | 0.5 | 2 | 29.5 | 78.1 |
| CEx 8.3 | 1 | 2 | 29.9 | 87.9 |
| CEx 8.4 | 0 | 2 | 30.4 | 91.8 |
| CEx 8.5 | 0 | 2 | 30.0 | 80.6 |
| Ex 8.12 | 0.5 | 2 | 29.3 | 72.4 |
| Ex 8.13 | 1 | 2 | 28.9 | 70.6 |
| Ex 8.14 | 0 | 2 | 30.3 | 91.6 |
| Ex 8.15 | 0 | 3 | 30.1 | 87.0 |

Examples 1-8 illustrate that SpeedCure® XKm can used to design photocurable initiation systems that take advantage of combined Norrish Type I and Type II reactivity with the same or better performance as those based on TPO, TPO-L and BAPO without the toxicity concerns associated with the latter three.

The invention claimed is:

1. A curable composition comprising:
   a) an ethylenically unsaturated compound consisting essentially of one or more (meth)acrylate-functionalized monomers and optionally one or more (meth)acrylate-functionalized oligomers; and
   b) a phosphine oxide photoinitiator having both Norrish Type I and Norrish type II activity.

2. The curable composition of claim 1, wherein the ethylenically unsaturated compound a) is selected from one or more (meth)acrylate-functionalized monomers, one or more (meth)acrylate-functionalized oligomers and mixtures thereof.

3. The curable composition of claim 2, wherein the one or more (meth)acrylate-functionalized monomers and/or the one or more (meth)acrylate-functionalized oligomers do not comprise any amino group.

4. The curable composition of claim 2, wherein the one or more (meth)acrylate functionalized monomers have 1 to 6 (meth)acrylate groups and a molecular weight of less than 600 g/mol.

5. The curable composition of claim 2, wherein the one or more (meth)acrylate functionalized monomers comprise a mono (meth)acrylate-functionalized monomer selected from the group consisting of methyl (meth)acrylate; ethyl (meth)acrylate; n-propyl (meth)acrylate; n-butyl (meth)acrylate; isobutyl (meth)acrylate; n-hexyl (meth)acrylate; 2-ethylhexyl (meth)acrylate; n-octyl (meth)acrylate; isooctyl (meth)acrylate; n-decyl (meth)acrylate; n-dodecyl (meth)acrylate; tridecyl (meth)acrylate; tetradecyl (meth)acrylate; hexadecyl (meth)acrylate; 2-hydroxyethyl (meth)acrylate; 2- and 3-hydroxypropyl (meth)acrylate; 2-methoxyethyl (meth)acrylate; 2-ethoxyethyl (meth)acrylate; 2- and 3-ethoxypropyl (meth)acrylate; tetrahydrofurfuryl (meth)acrylate; alkoxylated tetrahydrofurfuryl (meth)acrylate; 2-(2-ethoxyethoxy) ethyl (meth)acrylate; cyclohexyl (meth)acrylate; glycidyl (meth)acrylate; isodecyl (meth)acrylate; 2-phenoxyethyl (meth)acrylate; lauryl (meth)acrylate; alkoxylated phenol (meth)acrylates; alkoxylated nonylphenol (meth)acrylates; cyclic trimethylolpropane formal (meth)acrylate; isobornyl (meth)acrylate; tricyclodecanemethanol (meth)acrylate; tert-butylcyclohexanol (meth)acrylate; trimethylcyclohexanol (meth)acrylate; diethylene glycol monomethyl ether (meth)acrylate; diethylene glycol monoethyl ether (meth)acrylate; diethylene glycol monobutyl ether (meth)acrylate; triethylene glycol monoethyl ether (meth)acrylate; ethoxylated lauryl (meth)acrylate; methoxy polyethylene glycol (meth)acrylates; hydroxyl ethyl-butyl urethane (meth)acrylates; 3-(2-hydroxyalkyl) oxazolidinone (meth)acrylates; glycerol carbonate (meth)acrylate; and combinations thereof.

6. The curable composition of claim 2, wherein the composition comprises 10 to 80% by weight of the one or more (meth)acrylate-functionalized monomers based on the total weight of the curable composition.

7. The curable composition of claim 2, wherein the ethylenically unsaturated compound a) comprises the one or more (meth)acrylate-functionalized oligomers and the one or more (meth)acrylate functionalized oligomers have 1 to 18 (meth)acrylate groups and a number average molecular weight equal or more than 600 g/mol.

8. The curable composition of claim 2, wherein the ethylenically unsaturated compound a) comprises the one or more (meth)acrylate-functionalized oligomers and the one or more (meth)acrylate-functionalized oligomers are selected from the group consisting of (meth)acrylate-functionalized urethane oligomers, (meth)acrylate-functionalized epoxy oligomers, (meth)acrylate-functionalized polyether oligomers, (meth)acrylate-functionalized polydiene oligomers, (meth)acrylate-functionalized polycarbonate oligomers, (meth)acrylate-functionalized polyester oligomers and mixtures thereof.

9. The curable composition of claim 2, wherein the ethylenically unsaturated compound a) comprises the one or more (meth)acrylate-functionalized oligomers and the (meth)acrylate-functionalized oligomer comprises a (meth)acrylate-functionalized urethane oligomer having two (meth)acrylate groups.

10. The curable composition of claim 2, wherein the composition comprises 10 to 80% by weight of the one or more (meth)acrylate-functionalized oligomers based on the total weight of the curable composition.

11. The curable composition of claim 1, wherein the ethylenically unsaturated compound a) consists essentially of a mixture of one or more (meth)acrylate-functionalized monomers and one or more (meth)acrylate-functionalized oligomers.

12. The curable composition of claim 1, wherein the phosphine oxide photoinitiator b) has the following formula (I):

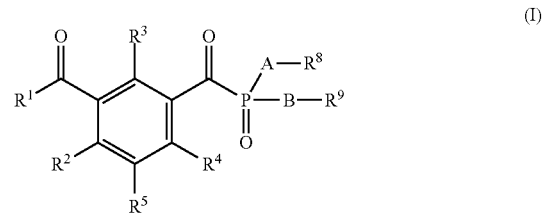

wherein
$R^1$ is $C_{1-20}$ alkyl, $C_7$-$C_{20}$ alkylaryl or an optionally substituted phenyl or polyphenyl;
$R^2$, $R^3$, $R^4$ and $R^5$ are independently hydrogen, halogen, $C_{1-20}$ alkyl, $-OR_6$ or $CF_3$ and two of radicals $R^2$, $R^3$, $R^4$ and $R^5$ may together form $C_{1-20}$ alkylene which can be interrupted by O, S or $NR_7$;
$R^6$ is hydrogen, $C_{1-20}$ alkyl, $C_{2-20}$ alkenyl, $C_3$-$C_8$ cycloalkyl, phenyl, benzyl or $C_{2-20}$ alkyl which is interrupted once or more than once by O or S and which is unsubstituted or is substituted by OH and/or SH;
$R^7$ is hydrogen, phenyl, $C_{1-12}$ alkyl or $C_{2-12}$ alkyl which is interrupted once or more than once by O or S and which is unsubstituted or substituted by OH and/or SH;
$R^8$ and $R^9$ are independently an optionally substituted group selected from $C_1$-$C_{20}$ alkyl, $C_1$-$C_{20}$ alkoxy, $C_{2-20}$ alkenyl, $C_3$-$C_8$ cycloalkyl, $C_6$-$C_{12}$ aryl, $C_7$-$C_{20}$ alkylaryl and $C_5$-$C_9$ heteroaryl;
A and B are independently a bond, $-(CH_2)_n-$ or $-C(=O)-$;
n is 1 to 10.

13. The curable composition of claim 12, wherein
$R^1$ is phenyl;
$R^2$, $R^3$ and $R^4$ are independently hydrogen, Cl, methyl or methoxy;
$R^5$ is hydrogen;
-A-$R^8$ and -B-$R^9$ are independently phenyl, methoxy, ethoxy, trimethylpentyl or a group of formula (II):

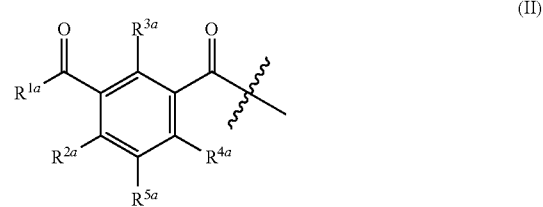

wherein
$R^{1a}$, $R^{2a}$, $R^{3a}$, $R^{4a}$ and $R^{5a}$ are respectively as defined for $R^1$, $R^2$, $R^3$, $R^4$ and $R^5$.

14. The curable composition of claim 1, wherein the phosphine oxide photoinitiator b) is selected from one of the following compounds:

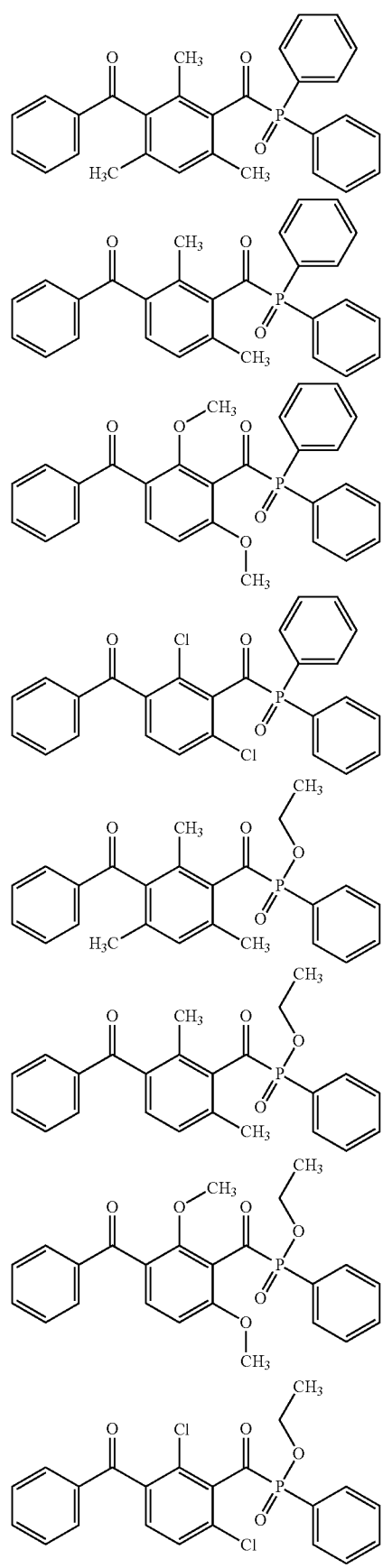
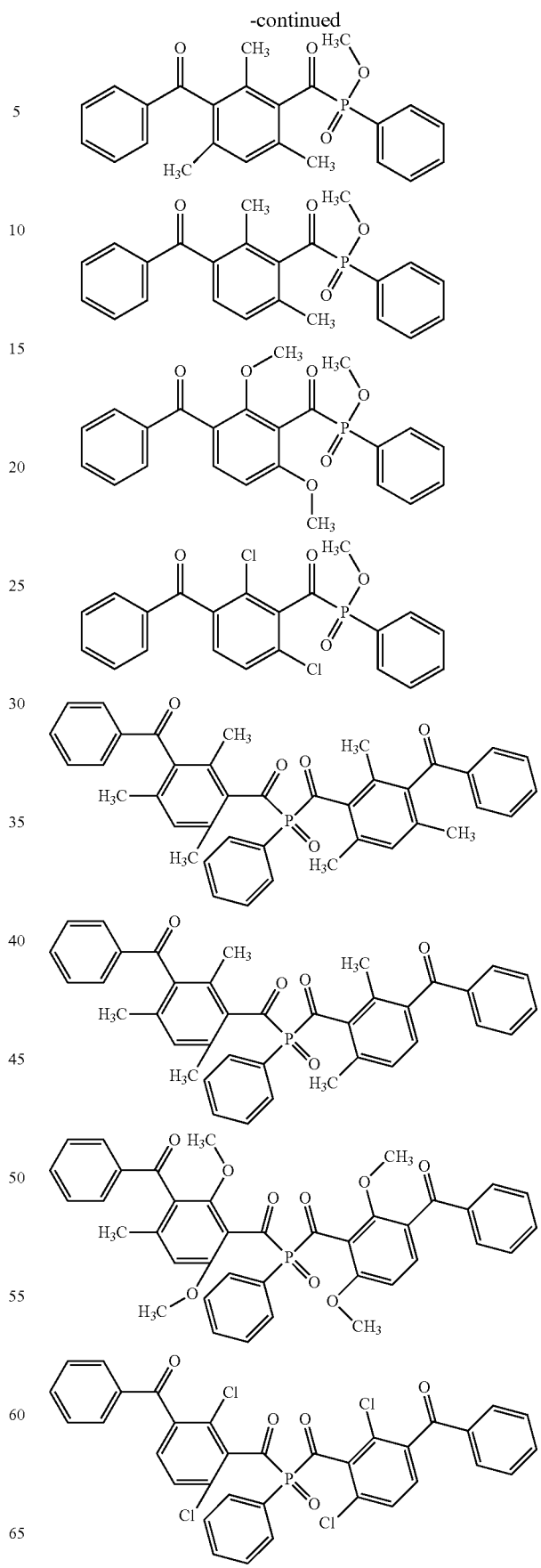

-continued

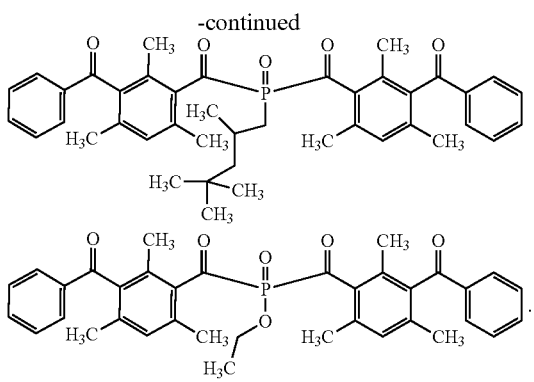

15. The curable composition of claim 1, wherein the composition comprises 0.05% to 10% by weight of phosphine oxide photoinitiator b) based on the total weight of the curable composition.

16. The curable composition of claim 1, wherein the composition further comprises a cationically polymerizable compound.

17. The curable composition of claim 1, wherein the composition further comprises a photoinitiator other than b) selected from the group consisting of benzoins, benzoin ethers, acetophenones, α-hydroxy acetophenones, benzyl, benzyl ketals, anthraquinones, phosphine oxides, acylphosphine oxides, α-hydroxyketones, phenylglyoxylates, α-aminoketones, benzophenones, thioxanthones, xanthones, acridine derivatives, phenazene derivatives, quinoxaline derivatives, triazine compounds, benzoyl formates, aromatic oximes, metallocenes, acylsilyl or acylgermanyl compounds, camphorquinones, polymeric derivatives thereof, a cationic photoinitiator, and mixtures thereof.

18. The curable composition of claim 17, wherein the photoinitiator other than b) comprises a thioxanthone.

19. The curable composition of claim 17, wherein the photoinitiator other than b) comprises a phenylglyoxylate.

20. The curable composition of claim 17, wherein the photoinitiator other than b) comprises a benzophenone.

21. The curable composition of claim 17, wherein the photoinitiator other than b) comprises a cationic photoinitiator selected from the group consisting of onium salts with anions of weak nucleophilicity; sulfoxonium salts; diazonium salts; metallocene salts; and mixtures thereof.

22. The curable composition of claim 1, wherein the composition further comprises an additive selected from the group consisting of sensitizers, amine synergists, stabilizers, antioxidants, light blockers, polymerization inhibitors, foam inhibitors, flow or leveling agents, colorants, pigments, dispersants, slip additives, fillers, chain transfer agents, thixotropic agents, matting agents, impact modifiers, waxes and mixtures thereof.

23. The curable composition of claim 1, wherein the composition is free of amine synergist.

24. A process for the preparation of a cured product, comprising curing the composition according to claim 1 by exposing the composition to radiation or to an electron beam.

25. The process of claim 24, wherein the process is for the preparation of a 3D-printed article and the process comprises printing a 3D article with the composition.

26. The process of claim 24, wherein the process is a process for coating nails and the process comprises applying the composition on a nail, and curing the composition on the nail.

27. A cured product obtained by curing the composition according to claim 1.

* * * * *